(12) United States Patent
Gogniat et al.

(10) Patent No.: US 11,291,661 B2
(45) Date of Patent: Apr. 5, 2022

(54) PHARMACEUTICAL COMPOSITION

(71) Applicant: NOVARTIS AG, Basel (CH)

(72) Inventors: Geoffrey Gogniat, Basel (CH); Saran Kumar, Edison, NJ (US); Ulrich Meier, Basel (CH); Mario Rentsch, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/815,183

(22) Filed: Mar. 11, 2020

(65) Prior Publication Data

US 2021/0169866 A1 Jun. 10, 2021

Related U.S. Application Data

(60) Provisional application No. 62/850,781, filed on May 21, 2019, provisional application No. 62/817,795, filed on Mar. 13, 2019.

(51) Int. Cl.
| | | |
|---|---|---|
| *A61K 31/46* | (2006.01) | |
| *A61P 1/16* | (2006.01) | |
| *A61K 9/00* | (2006.01) | |
| *A61K 9/16* | (2006.01) | |
| *A61K 9/20* | (2006.01) | |
| *A61K 9/28* | (2006.01) | |
| *A61K 9/48* | (2006.01) | |
| *A61K 9/50* | (2006.01) | |

(52) U.S. Cl.
CPC ............ *A61K 31/46* (2013.01); *A61K 9/0053* (2013.01); *A61K 9/1623* (2013.01); *A61K 9/1635* (2013.01); *A61K 9/1652* (2013.01); *A61K 9/2009* (2013.01); *A61K 9/2013* (2013.01); *A61K 9/2018* (2013.01); *A61K 9/2054* (2013.01); *A61K 9/2866* (2013.01); *A61K 9/485* (2013.01); *A61K 9/4825* (2013.01); *A61K 9/4858* (2013.01); *A61K 9/4866* (2013.01); *A61K 9/5047* (2013.01); *A61K 9/5089* (2013.01); *A61P 1/16* (2018.01)

(58) Field of Classification Search
CPC .... A61K 31/46; A61K 9/0053; A61K 9/1623; A61K 9/1635; A61K 9/1652; A61K 9/2009; A61K 9/2013; A61K 9/2018; A61K 9/2054; A61K 9/2866; A61K 9/4825; A61K 9/485; A61K 9/4858; A61K 9/4866; A61K 9/5047; A61K 9/5089; A61P 1/16
See application file for complete search history.

(56) References Cited

U.S. PATENT DOCUMENTS 10,077,268 B2 * 9/2018 Evans ................. C07D 403/06

OTHER PUBLICATIONS

Tully, David, C., et al., Discovery of Tropifexor (LJN452), a Highly Potent Non-bile Acid FXR Agonist for the Treatment of Cholestatic Liver Diseases and Nonalcoholic Steatohepatitis (NASH), Journal of Medicinal Chemistry, vol. 60, No. 24, Nov. 16, 2017, pp. 9960-9973.

* cited by examiner

*Primary Examiner* — Robert A Wax
*Assistant Examiner* — Olga V. Tcherkasskaya
(74) *Attorney, Agent, or Firm* — Francine F. Li

(57) ABSTRACT

The present invention relates to the field of pharmacy, particularly to a pharmaceutical composition for oral administration comprising an (a) inert substrate and a (b) mixture comprising a non-bile acid farnesoid X receptor (FXR) agonist, such as 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one binder. The present invention also relates to a process for preparing said pharmaceutical composition for oral administration; and to the use of said pharmaceutical composition in the manufacture of a medicament.

20 Claims, 15 Drawing Sheets

FIGURES
Figure 1: The manufacturing process for the pharmaceutical composition comprising Compound (A)
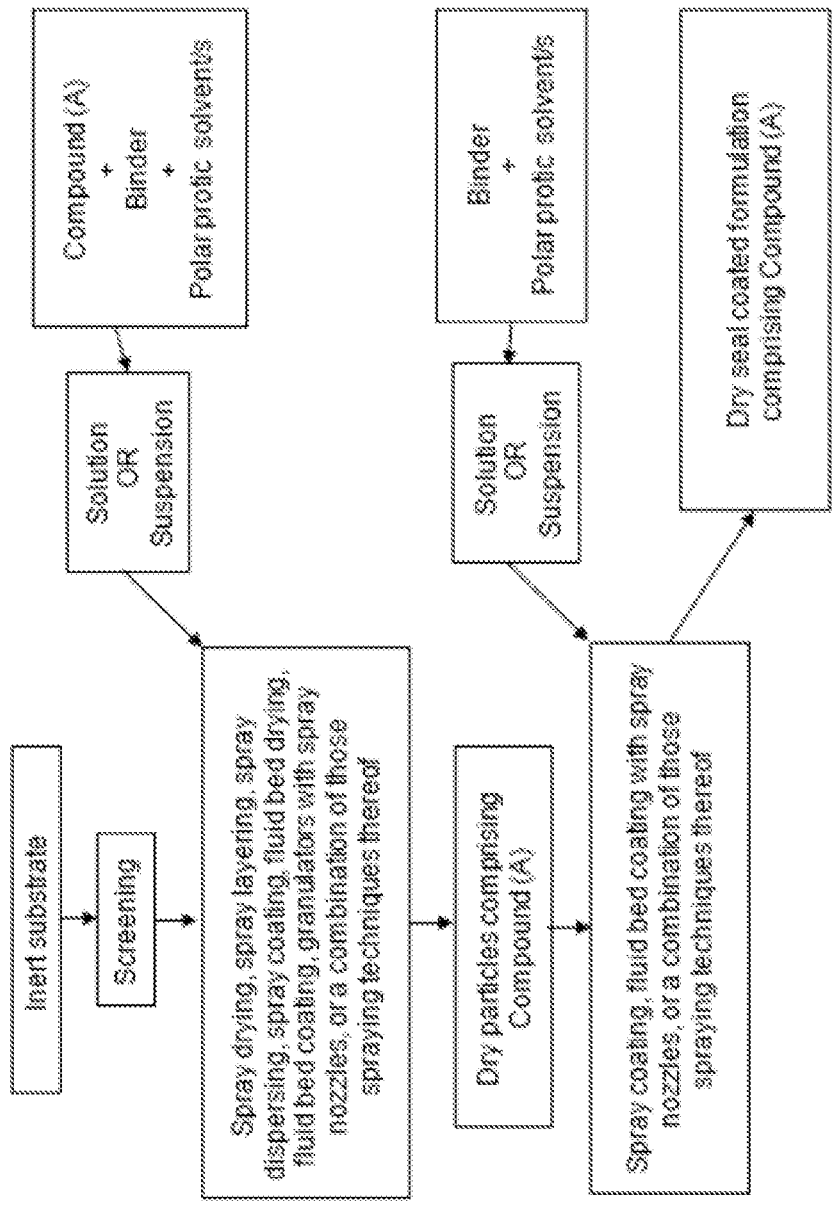

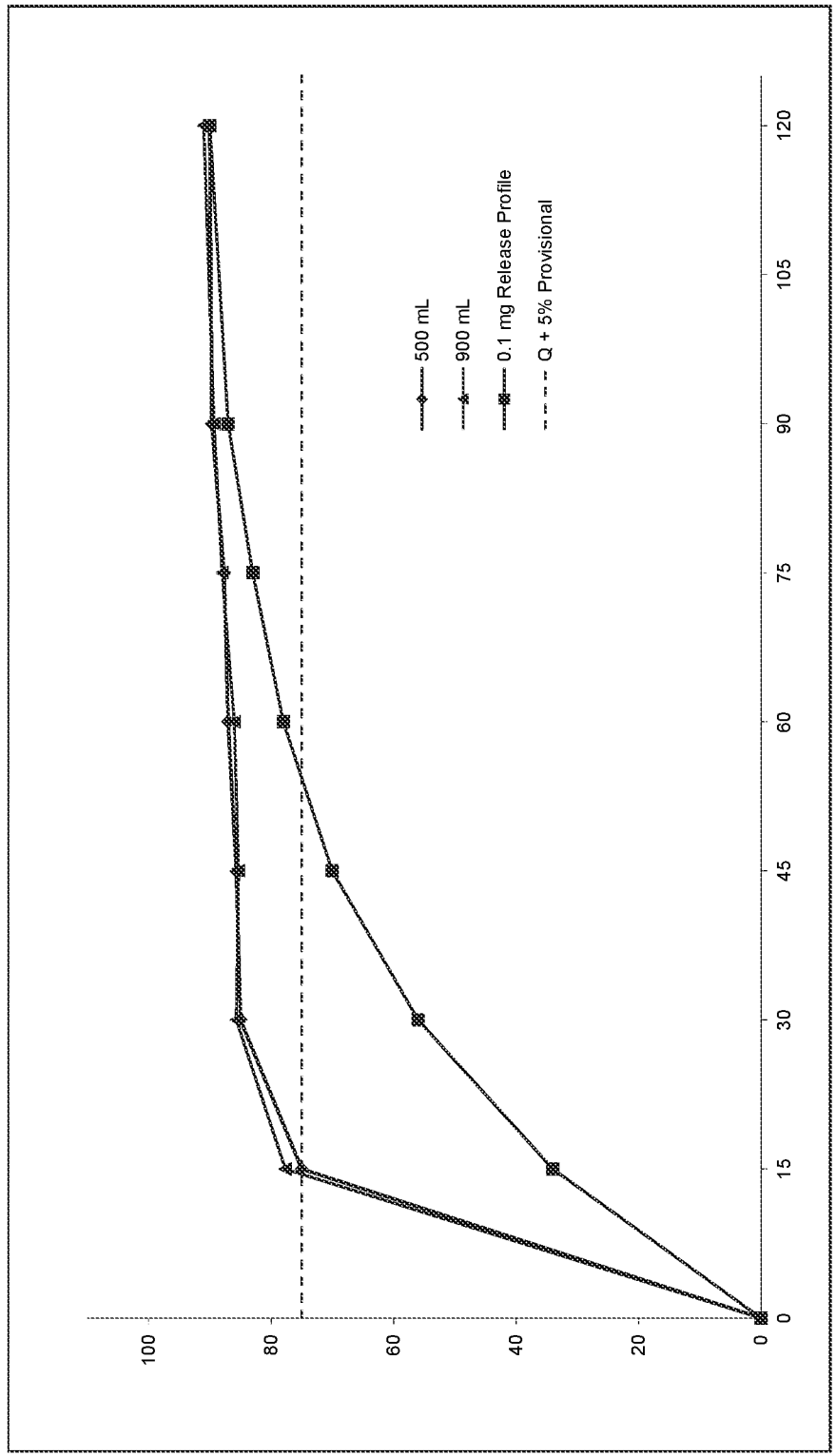
Figure 2: Dissolution profile for 0.03 mg of Capsule (C1) comprising Compound (A)

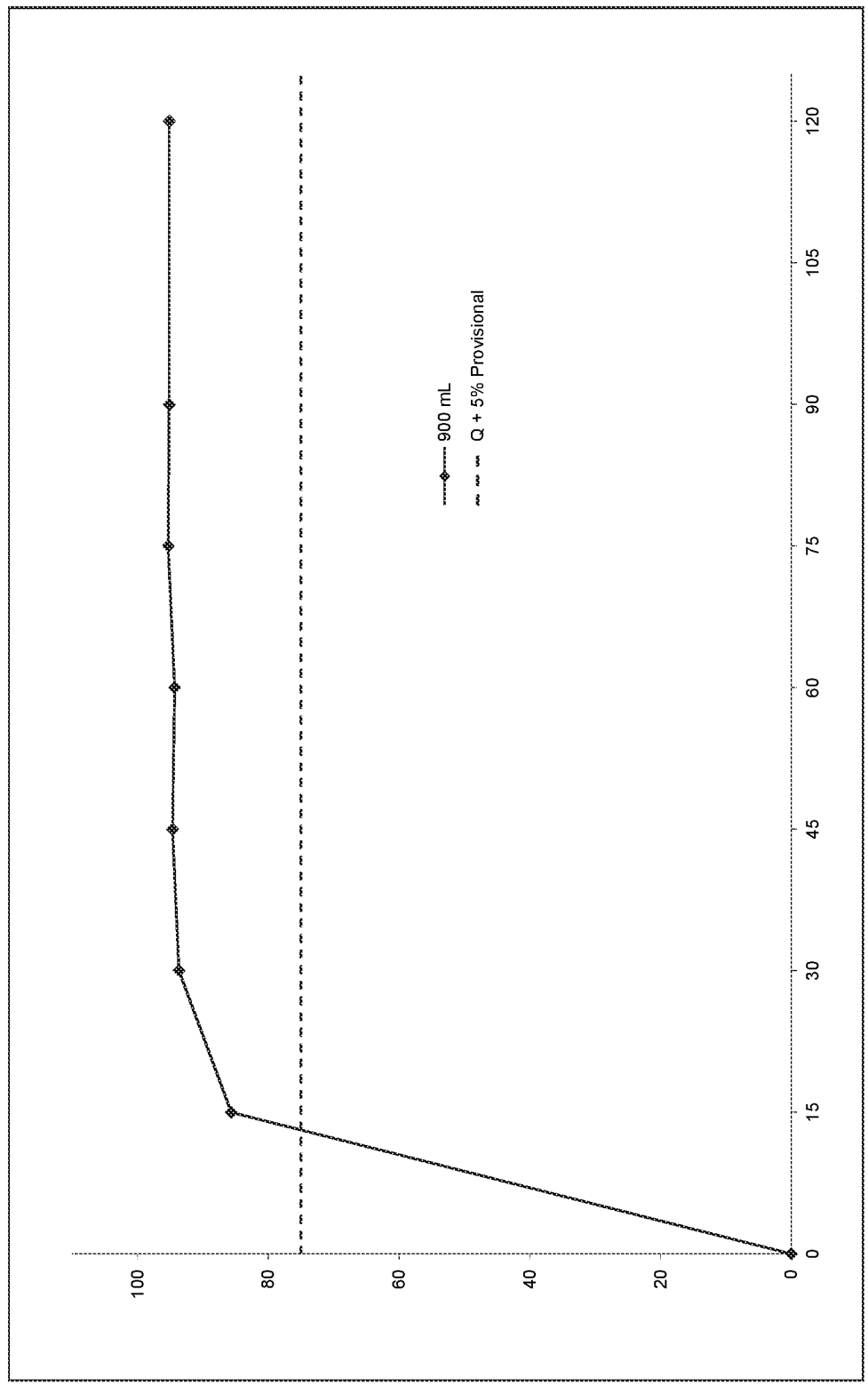

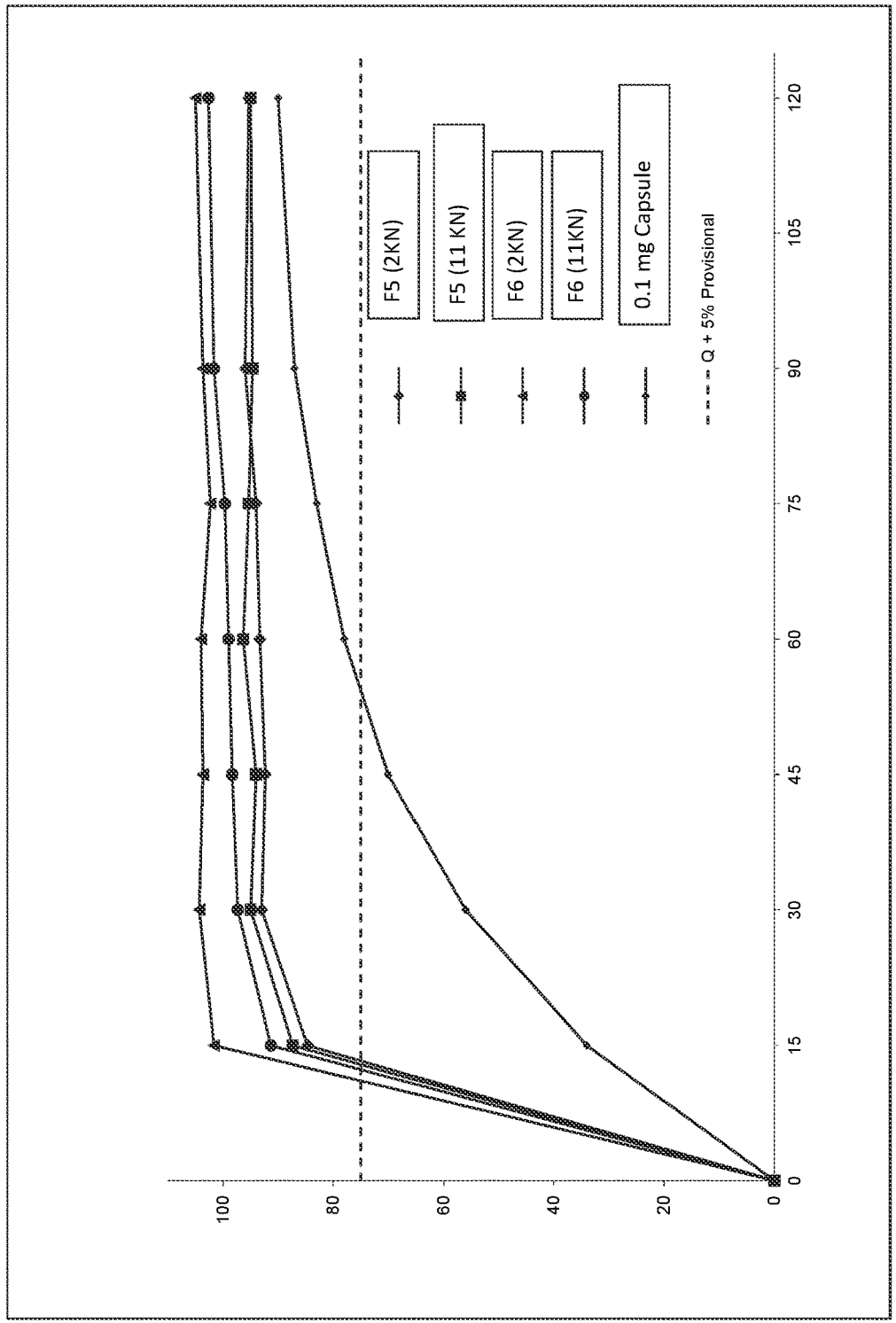
Figure 4: Dissolution profile for 0.03 mg Compound A tablets comprising Formulation 5 (F5) and Formulation 6 (F6) at different compression forces

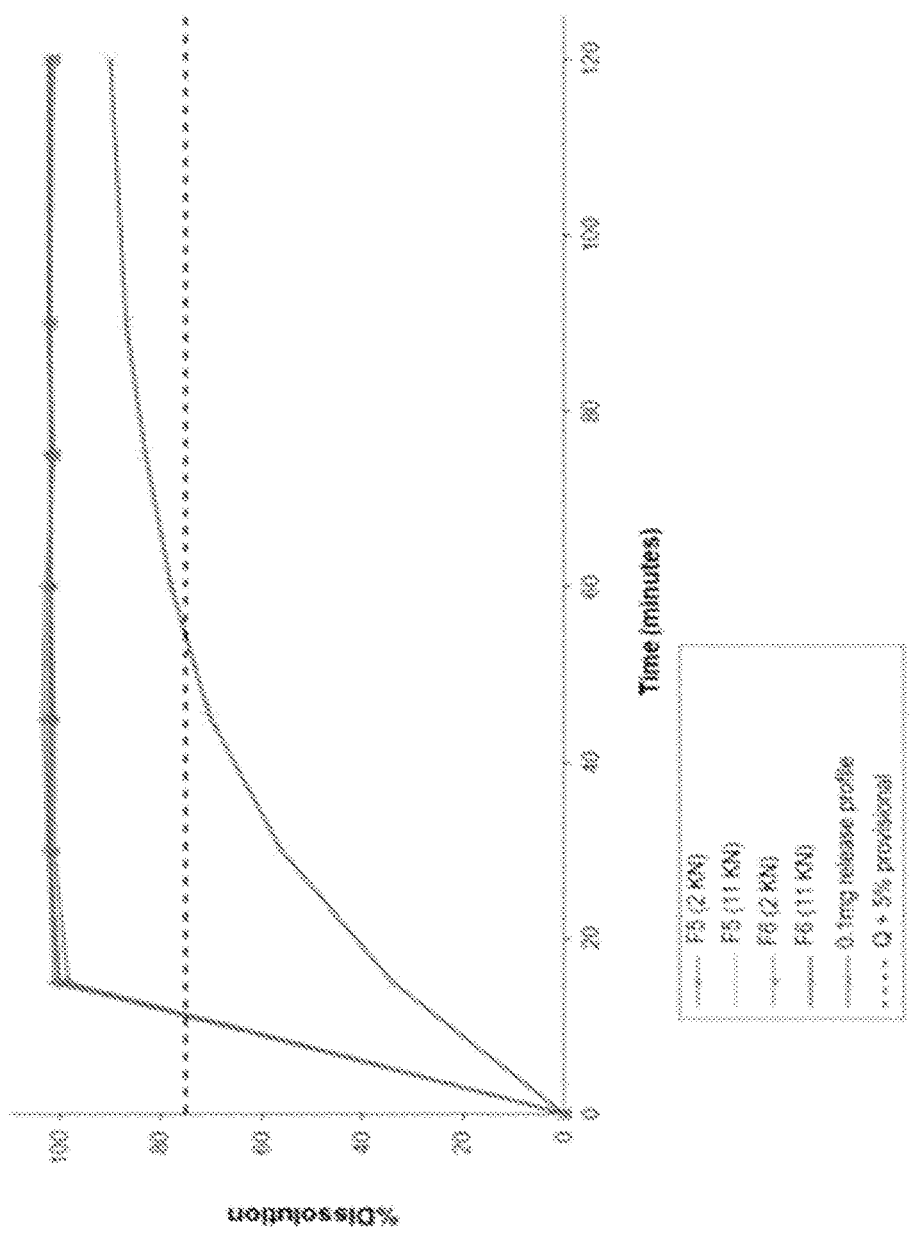
Figure 5: Dissolution profile for 0.16 mg Compound A tablets comprising Formulation 5 (F5) and Formulation 6 (F6) at different compression forces

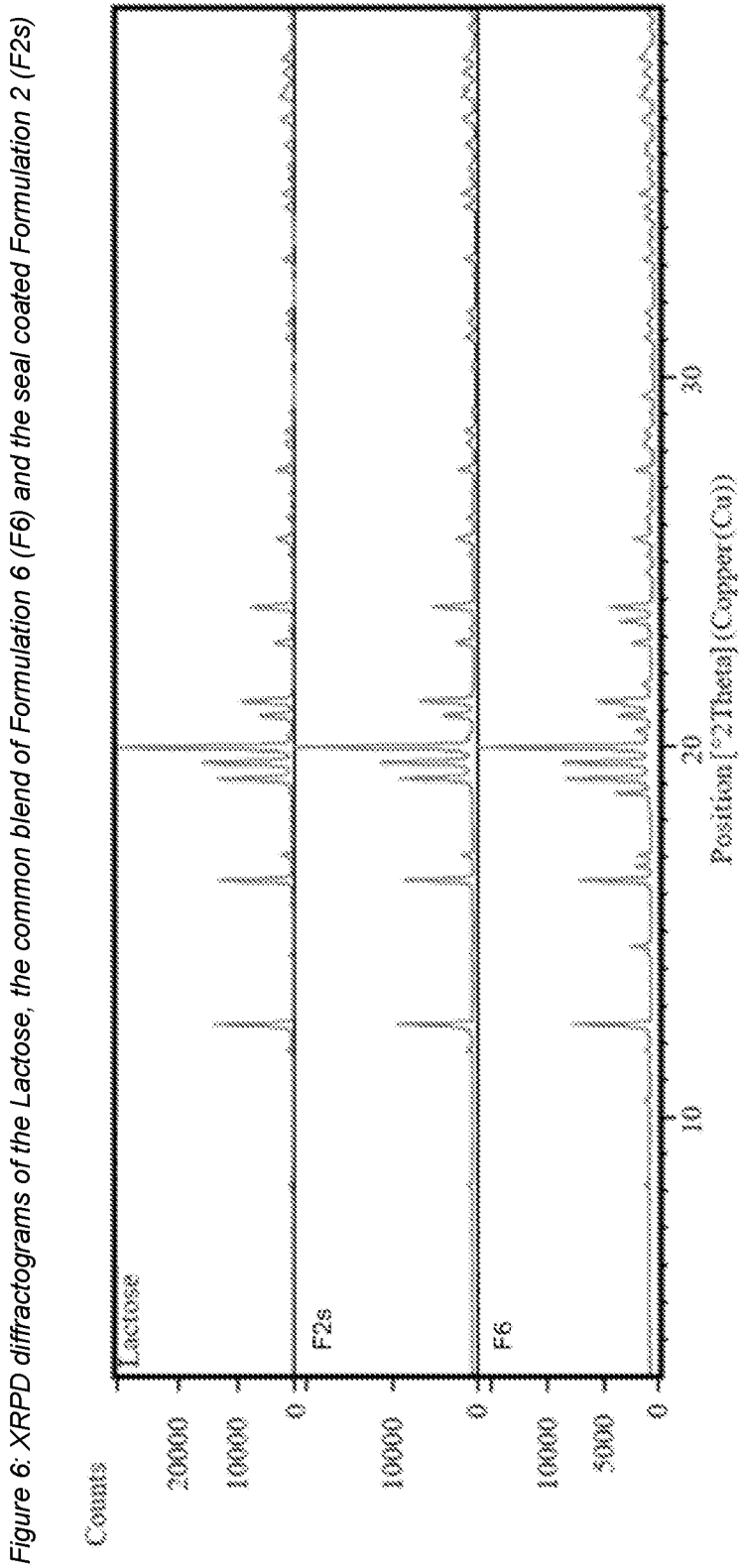
Figure 6: XRPD diffractograms of the Lactose, the common blend of Formulation 6 (F6) and the seal coated Formulation 2 (F2s)

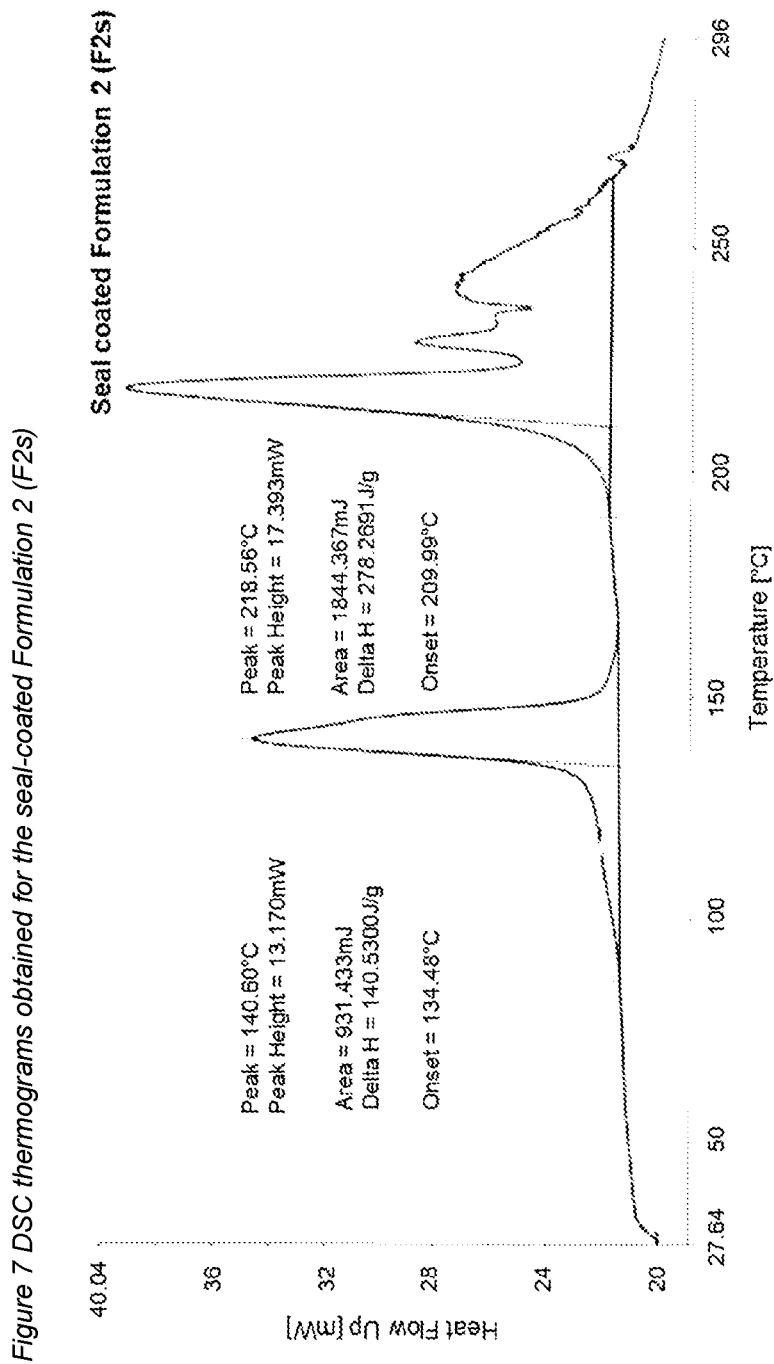
Figure 7 DSC thermograms obtained for the seal-coated Formulation 2 (F2s)

Figure 8: Particle size distribution (PSD) of the seal coated Formulation 2 (F2s)
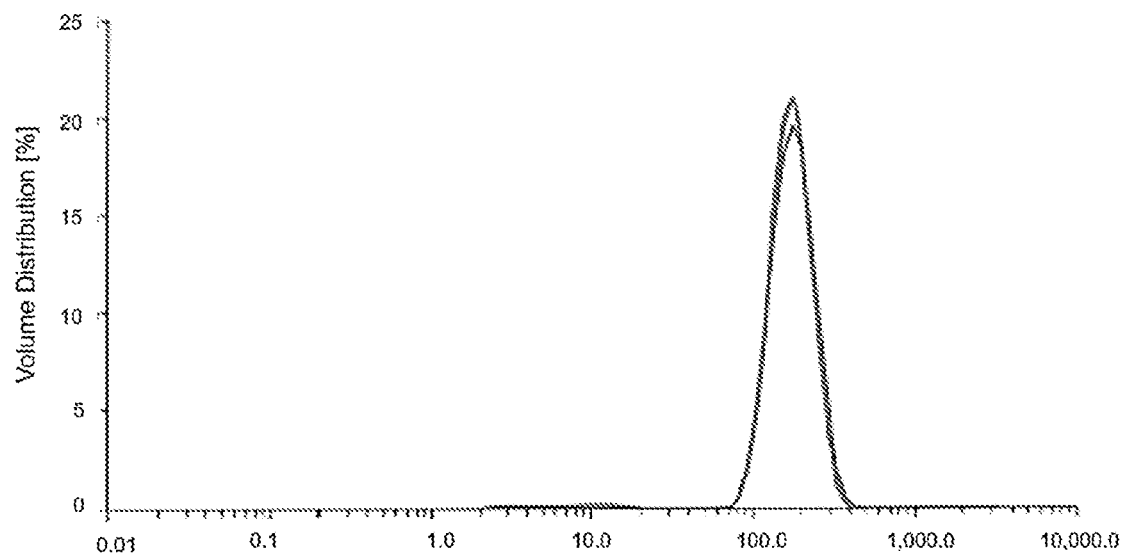
Figure 9: Particle size distribution (PSD) of the tablet blend of Formulation 6 (F6)
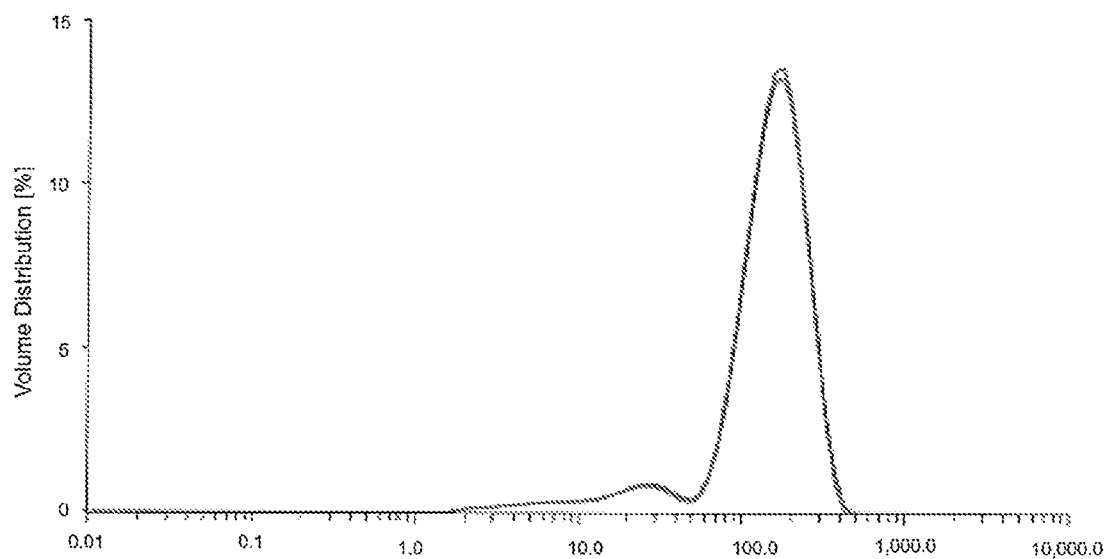

Figure 10: SEM of Lactose (inert substrate without Compound (A)) at 5 µm
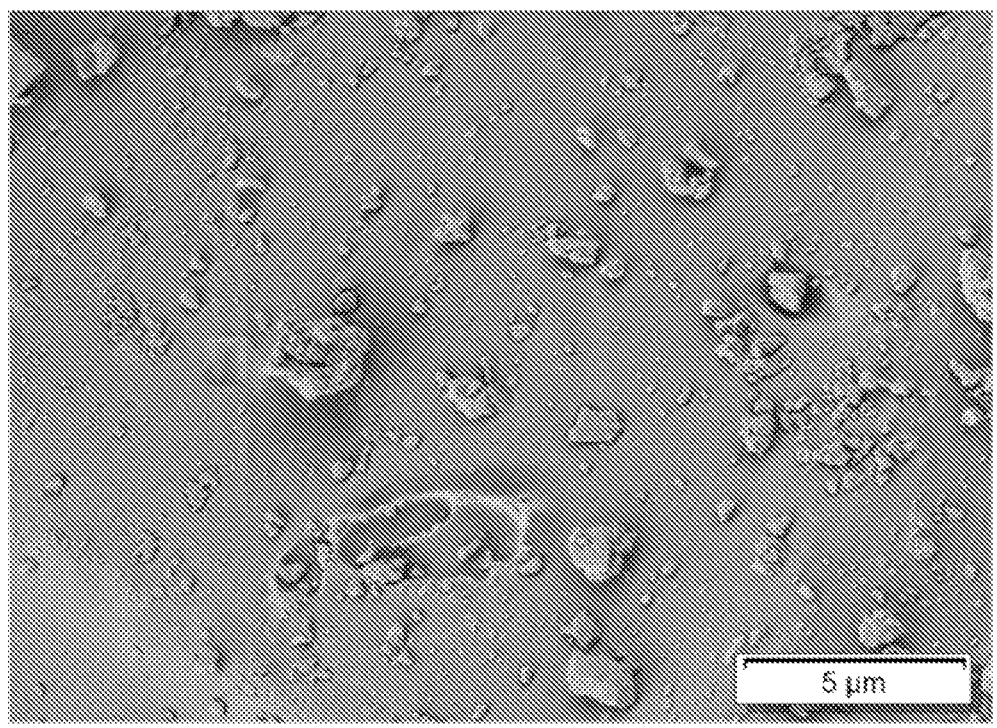
Figure 11: SEM analysis of the Formulation 2 (F2) at 5 µm
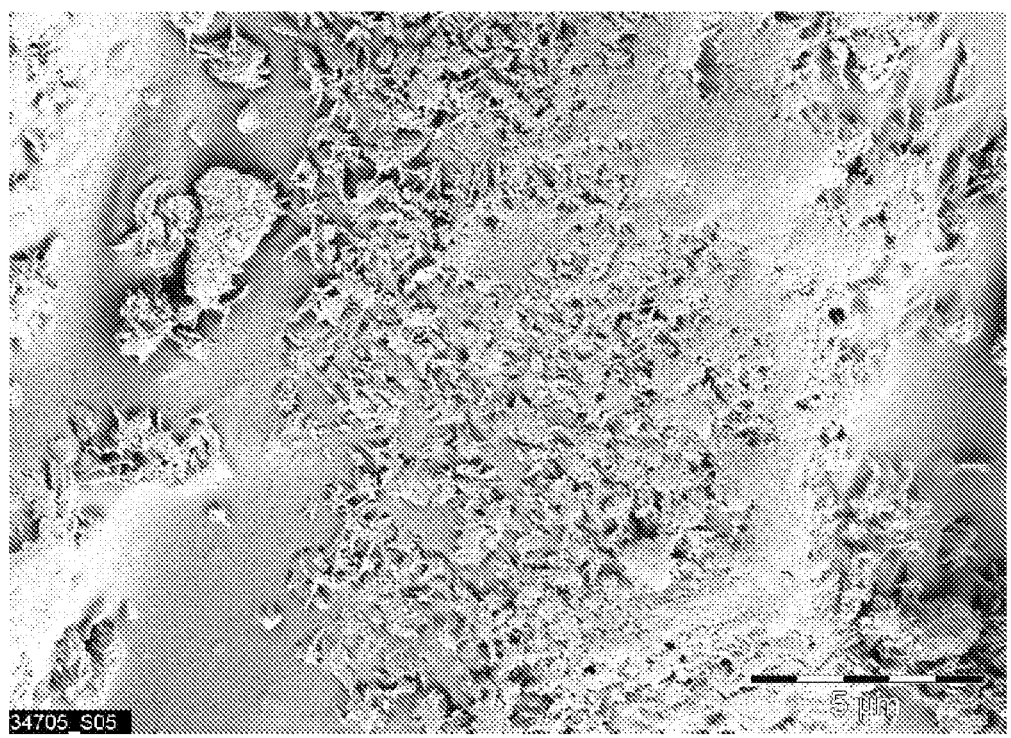

Figure 12: SEM analysis of the Formulation 2 (F2) at 100 μm
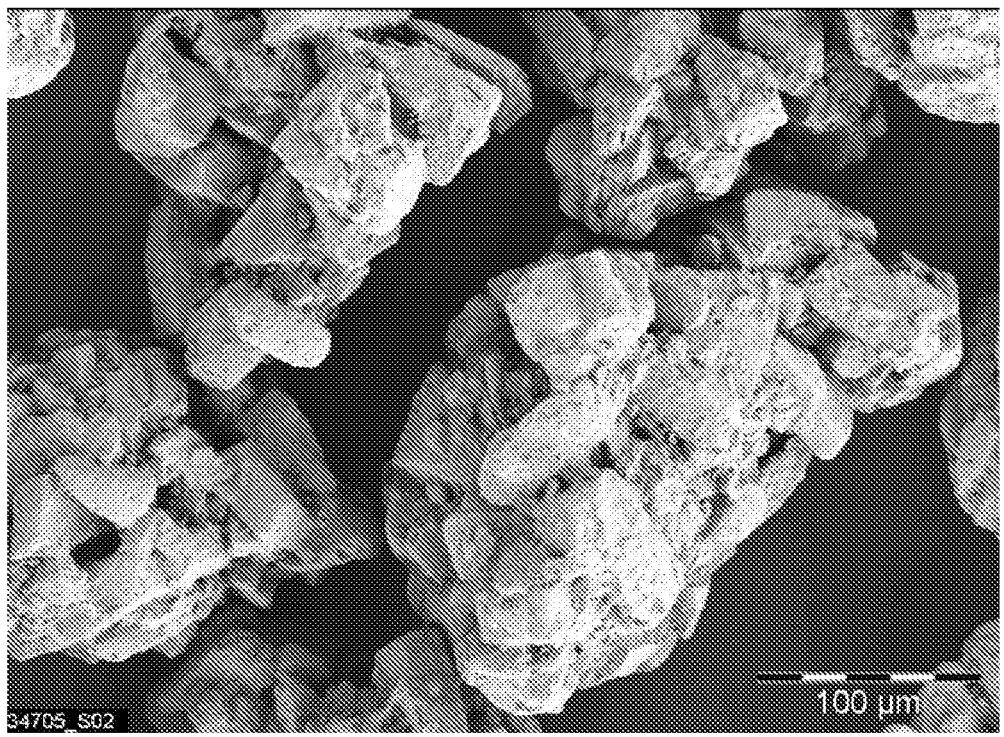
Figure 13: SEM analysis of the seal coated Formulation 2 (F2s) at 100 μm
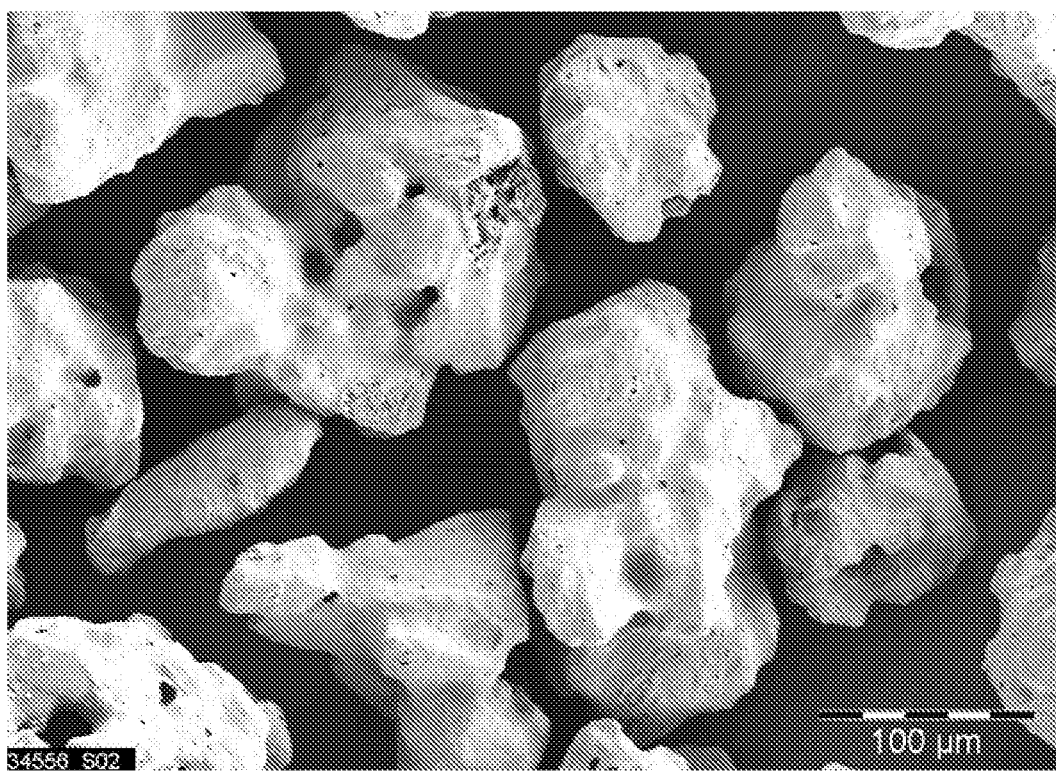

Figure 14: SEM analysis of the Formulation 2 (F2) at 20 μm
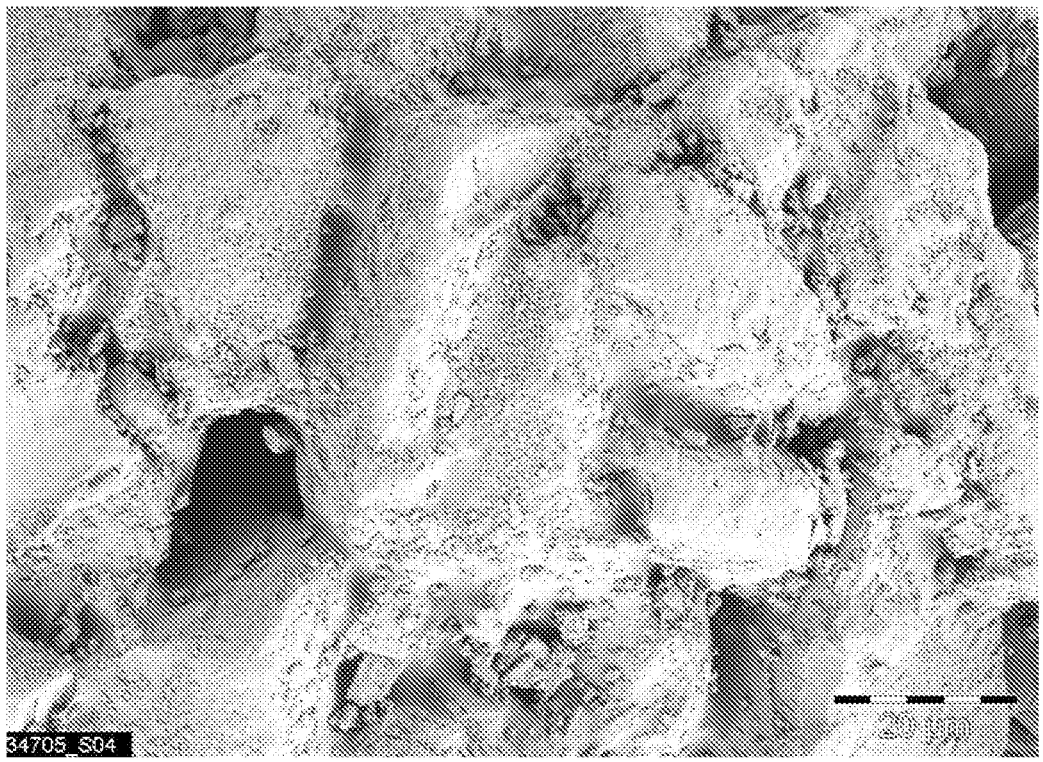
Figure 15: SEM analysis of the sealed coated Formulation 2 (F2s) at 20 μm
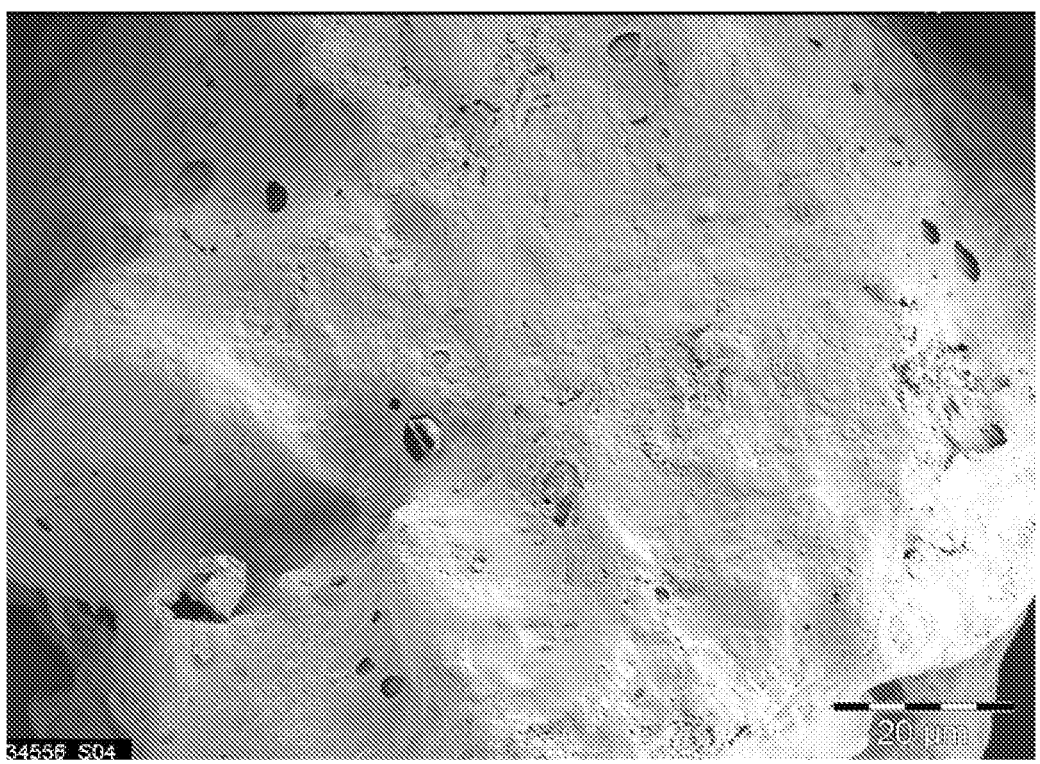

Figure 16: Surface Raman mapping of sealed coated Formulation 2 (F2s) at 10 μm resolution
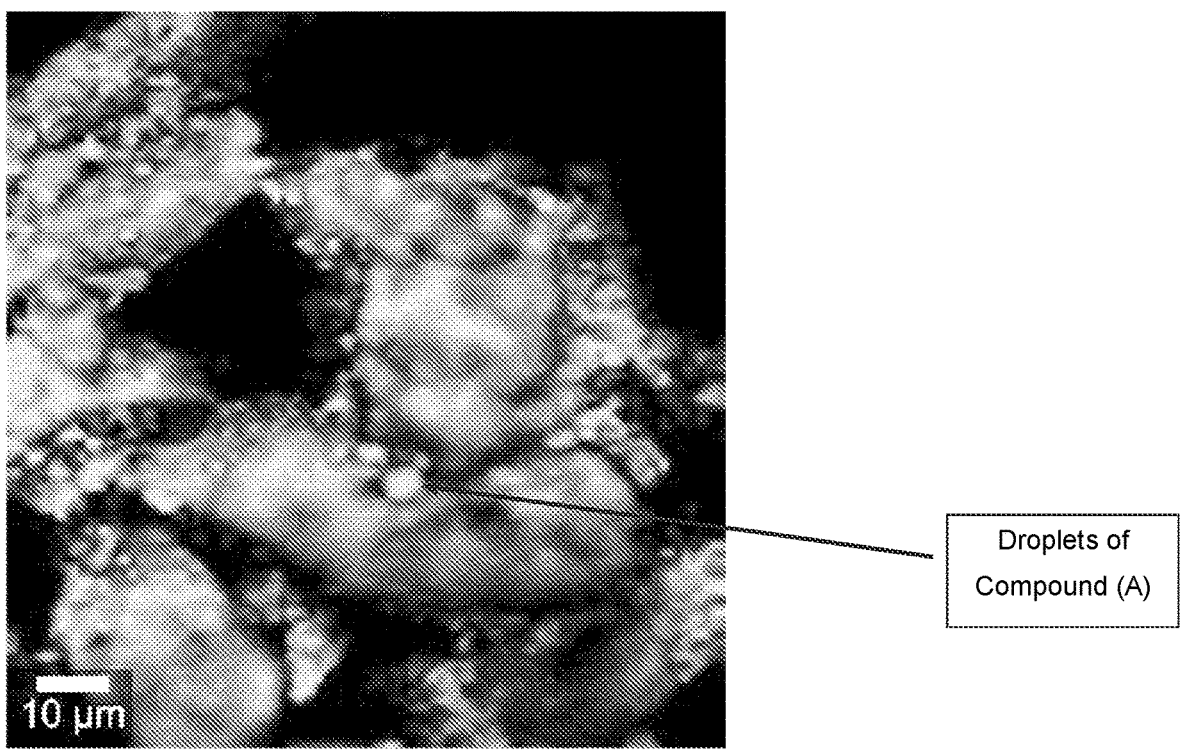

*Figure 17: Surface Raman mapping of sealed coated Formulation 2 (F2s) at 20 μm resolution*
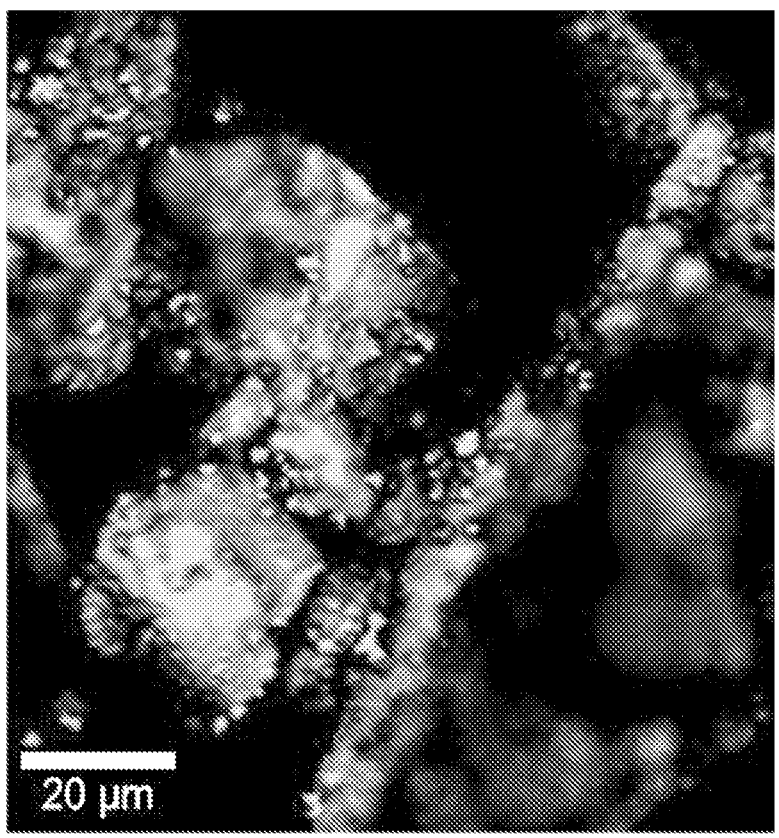

Figure 18: Raman spectra (0 - 1777 cm-1 range)
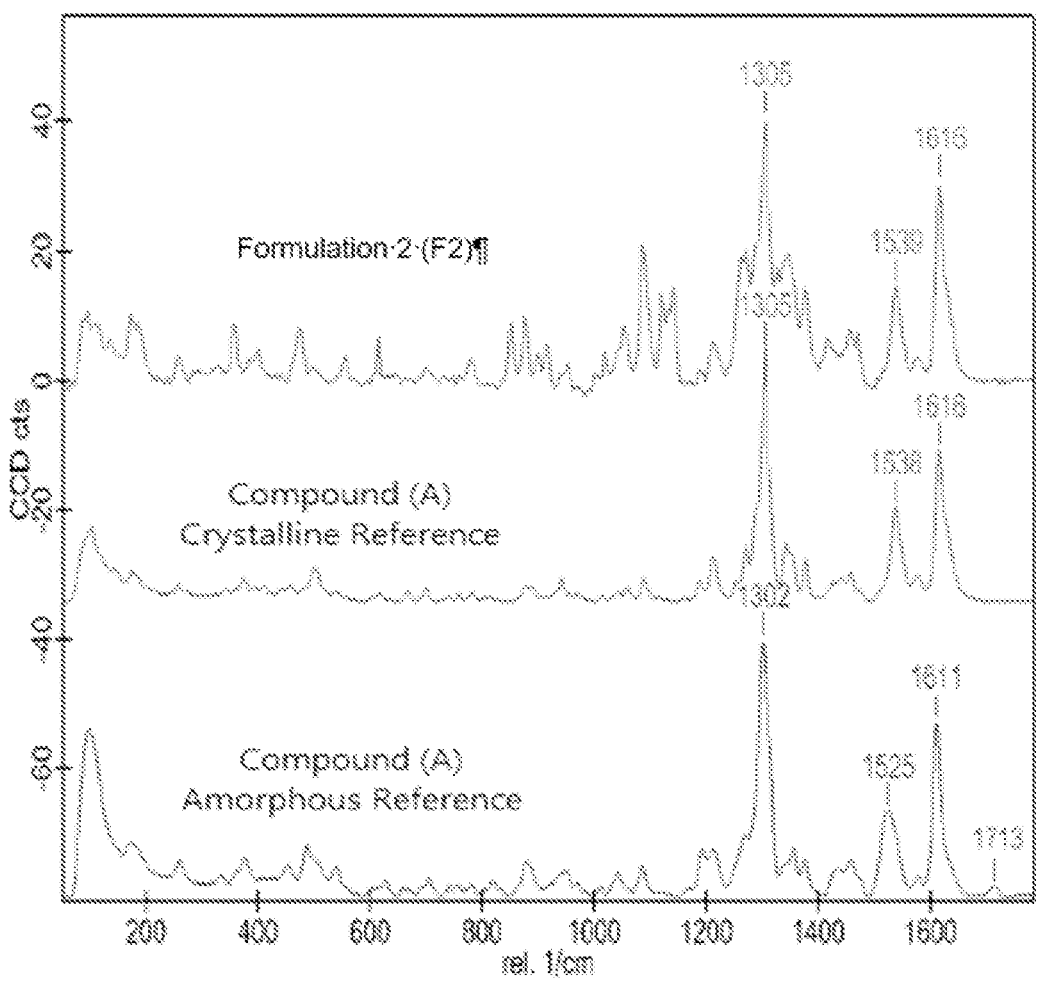

Figure 19: Average Plasma Concentration-Time Profiles for Compound (A) in Different Formulations in the Dog
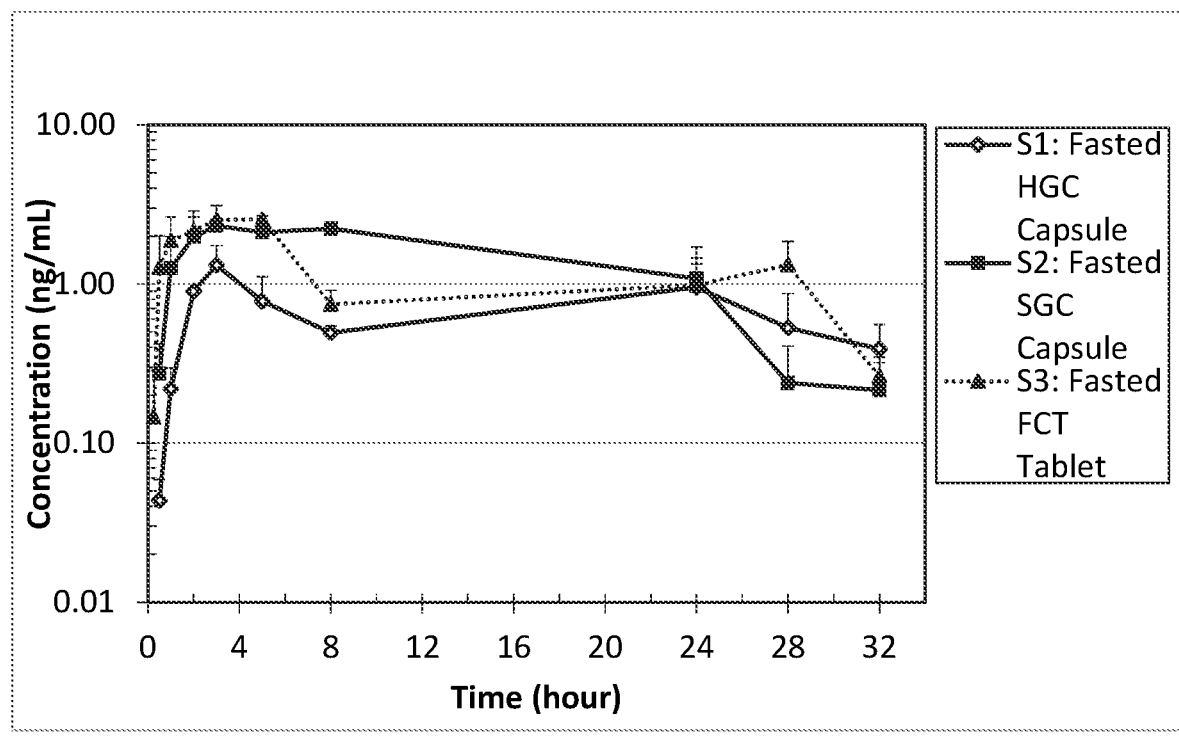

PHARMACEUTICAL COMPOSITION

FIELD OF THE INVENTION

The present invention relates to the field of pharmacy, particularly to a pharmaceutical composition for oral administration comprising particles, wherein said particles comprise an inert substrate, a mixture comprising a non-bile acid farnesoid X receptor (FXR) agonist, such as 2-[(1R,3r,5S)-3-({5-cyclopropyl-3-[2-(trifluoromethoxy)phenyl]-1,2-oxazol-4-yl}methoxy)-8-azabicyclo [3.2.1]octan-8-yl]-4-fluoro-1,3-benzothiazole-6-carboxylic acid, or a pharmaceutically acceptable salt thereof, and at least one binder. The present invention also relates to a pharmaceutical composition comprising a non-bile acid farnesoid X receptor (FXR) agonist, such as 2-[(1R,3r5S)-3-({5-cyclopropyl-3-[2-(trifluoromethoxy)phenyl]-1,2-oxazol-4-yl}methoxy)-8-azabicyclo [3.2.1]octan-8-yl]-4-fluoro-1,3-benzothiazole-6-carboxylic acid or a pharmaceutically acceptable salt thereof, and another active pharmaceutical ingredient. The present invention also relates to a process for preparing said pharmaceutical composition for oral administration; and to the use of said pharmaceutical composition in the manufacture of a medicament.

BACKGROUND OF THE INVENTION

Nuclear receptors constitute a superfamily of transcriptional regulatory proteins that share structural and functional properties and function as receptors for example steroids, retinoids, vitamin D, and thyroid hormones (Evans et al. *Science* 1988, 240, 889). The farnesoid X receptor (FXR) is a member of the nuclear hormone receptor superfamily and is primarily expressed in the liver, kidney and intestine (Seol et al. *Mol. Endocrinol.* 1995, 9, 72-85; Forman et al. Cell 1995, 81, 687-693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (Makishima et al. *Science* 1999, 284, 1362-1365; Parks et al. *Science* 1999, 284, 1365-1368; Wang et al. *Mol. Cell* 1999, 3, 543-553), which serve to inhibit cholesterol catabolism (Urizar et al. *J. Biol. Chem.* 2000, 275, 39313-39317). FXR agonists have been explored as therapeutics against non-alcoholic steatohepatitis (NASH).

The specific non-bile acid FXR agonist 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole -6-carboxylic acid, or a pharmaceutically acceptable salt thereof, is referred to herein as Compound (A). The present invention also relates to:

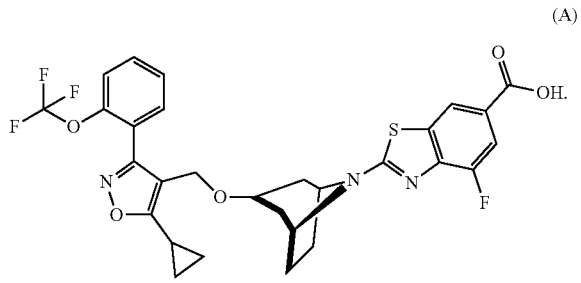

(A)

The compound was disclosed for the first time in WO 2012/087519 (Example 1, compound 1-IB of the table on page 125) and it is also known under the name LJN452 and under its International Nonproprietary Name (INN) "Tropifexor". Said compound may be used for the treatment of an FXR mediated disease or disorder. There is a need to provide a commercially viable pharmaceutical composition comprising 2-[(1R,3r,5S)-3-({5-cyclopropyl-3-[2-(trifluoromethoxy)phenyl]-1,2-oxazol-4-yl}methoxy)-8-azabicyclo [3.2.1]octan-8-yl]-4-fluoro-1,3-benzothiazole -6-carboxylic acid, or a pharmaceutically acceptable salt thereof.

In addition, the following classes of compounds or therapeutics have been explored to mediate metabolic dysfunctions: glucagon-like peptide 1 (GLP-1) receptor agonists (GLP-1RAs) and dipeptidyl peptidase-4 (DPP4) inhibitors, peroxisome proliferator-activated receptor (PPARs) agonists, acetyl-CoA carboxylase (ACC) inhibitors, thyroid hormone receptor β (TRβ) agonists, ketohexokinase (KHK) inhibitors, diacylglycerol Acyltransferase 2 (DGAT2) inhibitors, and sodium-glucose linked transporter (SGLT) inhibitors.

Other related targets and agents include: anti-inflammatory agents (such as chemokine receptor 2/5 (CCR2/5) antagonists), and anti-fibrosis agents (such as Galectin-3 inhibitors and Lysyl oxidase-like 2 (LOXL 2) inhibitors).

Because the pathophysiology of NAFLD and NASH is complex and multiple redundant pathways may be implicated, there is a need to provide treatments for nonalcoholic fatty liver disease (NAFLD), NASH and fibrotic/cirrhotic that can address the different aspects of these complex conditions, while demonstrating an acceptable safety and/or tolerability profile.

BRIEF DESCRIPTION OF THE FIGURES

FIG. 1 shows the manufacturing process for the pharmaceutical composition comprising Compound (A).

FIG. 2 shows the dissolution profile for Capsule (C1) comprising 0.03 mg Compound (A), as disclosed herein, (500 mL and 900 mL vessels volume).

FIG. 3 shows the dissolution profile for Capsule (C2) comprising 0.16 mg Compound (A) (900 mL vessels volume).

FIG. 4 shows the dissolution profile for tablets comprising Formulation 5 (F5) and Formulation 6 (F6) with 0.03 mg of Compound (A), as disclosed herein, compressed at lowest and highest compression forces relative to the dry blend capsule formulation (0.1 mg release profile).

FIG. 5 shows the dissolution profile for tablets comprising Formulation 5 (F5) and Formulation 6 (F6) with 0.03 mg of Compound (A), as disclosed herein, compressed at lowest and highest compression forces relative to the dry blend capsule formulation (0.1 mg release profile).

FIG. 6 shows the XRPD diffractograms of the lactose, the common blend of Formulation 6 (F6) and the seal coated Formulation 2 (F2s).

FIG. 7 shows the DSC thermograms obtained for the seal coated Formulation 2 (F2s).

FIG. 8 shows the particle size distribution (PSP) of the seal coated Formulation 2 (F2s).

FIG. 9 shows the particle size distribution (PSP) of the tablet blend of Formulation 6 (F6) of the sealed coated tablet formulation comprising Compound (A).

FIG. 10 shows the SEM analysis of Lactose (inert substrate without Compound (A)) at 5 μm.

FIG. 11 shows the SEM analysis of the Formulation 2 (F2) at 5 μm.

FIG. 12 shows the SEM analysis of the Formulation 2 (F2) at 100 μm

FIG. 13 shows the SEM analysis of the seal coated Formulation 2 (F2s) at 100 μm.

FIG. 14 shows the SEM analysis of the Formulation 2 (F2s) at 20 μm.

FIG. 15 shows the SEM analysis of the sealed coated Formulation 2 (F2s) at 20 μm.

FIG. 16 shows the surface Raman mapping of the sealed coated Formulation 2 (F2s) at 10 μm resolution.

FIG. 17 shows the surface Raman mapping of sealed coated Formulation 2 (F2s) at 20 μm resolution.

FIG. 18 shows the Raman Spectra comparing crystalline and amorphous Compound (A), with Compound (A) in the Formulation 2 (F2) (0-1777 $cm^{-1}$ range).

FIG. 19 shows the average plasma concentration over time for Compound (A) in different formulations in the dog.

SUMMARY OF THE INVENTION

The design of a pharmaceutical composition, a pharmaceutical dosage form, as well as a commercially viable process to prepare the pharmaceutical composition, for a non-bile acid FXR agonist, such as 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof (herein Compound (A)) is especially challenging. This non-bile acid FXR agonist is a highly potent active pharmaceutical ingredient (API) classified by the biopharmaceutical classification system as a class IV compound, e.g. poorly soluble and poorly permeable compound. Moreover, this non-bile acid FXR agonist is difficult to formulate due to its physicochemical properties and its high potency. Finding a suitable pharmaceutical composition, in a reliable and robust way, proved challenging. For example, due to its very high potency a low dosage is needed (sub-milligrams or micrograms), generating unwanted formulation issues such as content uniformity, and additional manufacturing difficulties, particularly when practiced on a larger manufacturing scale. Furthermore, this non-bile acid FXR agonist has a low water solubility and mixing the compound with conventional excipients to provide an effective composition proved difficult (owing to instability of the formulation, unpredictable dissolution rates and variable bioavailability). Accordingly, a suitable and robust solid pharmaceutical composition overcoming the above problems needs to be developed.

In view of the above-mentioned difficulties, and considerations, it was surprising to find a way to prepare a stable pharmaceutical composition that allows the preparation of a pharmaceutical composition comprising low amounts of the active compound, avoiding any content uniformity or manufacturing issues.

In one aspect the present invention relates to a pharmaceutical composition for oral administration comprising (a) an inert substrate, and (b) a mixture comprising 2-[(1R,3r, 5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one binder.

In one aspect the present invention relates to a pharmaceutical composition for oral administration comprising particles, wherein said particles comprise (a) an inert substrate, and (b) a mixture comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1, 3-benzothiazole-6-carboxylic acid, or a pharmaceutically acceptable salt thereof, and at least one binder.

Aspects, advantageous features and preferred embodiments of the present invention summarized in the following items, respectively alone or in combination, contribute to solving the object of the invention.

Item A1. A pharmaceutical composition for oral administration comprising particles, wherein said particles comprise (a) an inert substrate, and (b) a mixture comprising 2-[(1R,3r,5S) -3-({5-cyclopropyl-3-[2-(trifluoromethoxy) phenyl]-1,2-oxazol-4-yl}methoxy)-8-aza bicyclo[3.2.1]octan-8-yl]-4-fluoro-1,3-benzothiazole-6-carboxylic acid, or a pharmaceutically acceptable salt thereof, and at least one binder.

Item A2. The pharmaceutical composition according to item A1, wherein 2-[(1R,3r,5S)-3-({5-cyclopropyl-3-[2-(trifluoromethoxy)phenyl]-1,2-oxazol-4-yl}methoxy)-8-azabicyclo[3.2.1] octan-8-yl]-4-fluoro-1,3-benzothiazole-6-carboxylic acid, or a pharmaceutically acceptable salt thereof, is in amorphous form, crystalline form, or a mixture thereof.

Item A3. The pharmaceutical composition according to item A1 to A2, wherein 2-[(1R,3r,5S)-3-({5-cyclopropyl-3-[2-(trifluoromethoxy)phenyl]-1,2-oxazol-4-yl}methoxy)-8-azabicyclo[3.2.1] octan-8-yl]-4-fluoro-1,3-benzothiazole-6-carboxylic acid is a free form.

Item A4. The pharmaceutical composition according to items A1 to A3, wherein the (b) mixture comprising 2-[(1R, 3r,5S)-3-({5-cyclopropyl-3-[2-(trifluoromethoxy)phenyl]-1, 2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one binder, is dispersed onto the (a) inert substrate.

Item A5. The pharmaceutical composition according to items A1 to A3, wherein the (a) inert substrate is coated with the (b) mixture comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole -6-carboxylic acid, or a pharmaceutically acceptable salt thereof, and at least one binder.

Item A6. The pharmaceutical composition according to any one of items A1 to A5, wherein the (a) inert substrate comprises a material which is selected from the group consisting of lactose, microcrystalline cellulose, mannitol, sucrose, starch, granulated hydrophilic fumed silica, or mixtures thereof.

Item A7. The pharmaceutical composition according to any one of items A1 to A6, wherein the binder is selected from the group consisting of polyvinyl pyrrolidone, hydroxypropyl cellulose, hypromellose, carboxymethyl cellulose, methyl cellulose, hydroxyethyl cellulose, carboxyethyl cellulose, carboxymethylhydroxyethyl cellulose, polyethylene glycol, polyvinylalcohol, shellac, polyvinyl alcohol-polyethylene glycol co-polymer, or a mixtures thereof.

Item A8. The pharmaceutical composition according to any one of items A1 to A7, wherein the particles further comprises an outer (c) seal coating layer.

Item A9. The pharmaceutical composition according to any one of items A1 to A8, wherein the outer (c) seal coating layer is selected from the group consisting of hydroxypropyl methyl cellulose, polyvinyl pyrrolidone, hydroxypropyl cellulose, carboxymethyl cellulose, methyl cellulose, hydroxyethyl cellulose, carboxyethyl cellulose, carboxymethylhydroxyethyl cellulose, polyethylene glycol, polyvinylalcohol, or mixtures thereof.

Item A10. The pharmaceutical composition according to any one of items A1 to A9, wherein the particles are further formulated into a final dosage form, optionally in the presence of at least one pharmaceutically acceptable excipient, and wherein said final dosage form is a capsule, a tablet, a mini-tablet, a sachet, or a stickpack.

Item A11. The pharmaceutical composition according to item A10, wherein the final dosage form is a capsule or a tablet.

Item A12. The pharmaceutical composition according to any one of items A1 to A11, comprising at least one further active pharmaceutical ingredient.

Item A13. The pharmaceutical composition according to any one of items A1 to A12, wherein the final dosage form comprises 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole -6-carboxylic acid, or a pharmaceutically acceptable salt thereof, in an amount of about 0.01 mg to about 2 mg.

Item A14. A process for preparing the pharmaceutical composition for oral administration, as defined in items A1 to A13, said process comprising the steps of:
 (i) Mixing the (b) mixture comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro -1,3-benzothiazole-6-carboxylic acid, or a pharmaceutically acceptable salt thereof, with at least one binder, and optionally with at least one polar protic solvent, and
 (ii) Adding said mixture (i) to the (a) inert substrate of the particles.

Item A15. The process according to item A14, wherein the at least one protic polar solvent is selected from the group consisting of organic solvents, water, or mixtures thereof.

Item A16. The process according to item A15, wherein the organic solvent is selected from the group consisting of methanol, ethanol, isopropanol, n-propanol, n-butanol, or mixtures thereof.

Item A17. The process according to item A16, wherein the organic solvent is ethanol.

Item A18. The process according to items A14 to A17, wherein the solvent is removed at a temperature of 20° C. to 130° C.

Item A19. The process according to items A14 to A18, wherein the mixture of step (i) is dispersed onto the (a) inert substrate.

Item A20. The process according to any one of items A14 to A18, wherein the (a) inert substrate is coated with the mixture of step (i).

Item A21. The process according to any one of items A14 to A20, further comprising the step of adding an outer (c) seal coating layer onto said particles.

Item A22. The process according to any one of items A14 to A21, comprising the step of further adding at least one additional active pharmaceutical ingredient.

Items A23. The process according to any one of items A14 to A22, further comprising preparing the final dosage form by optionally mixing the particles with at least one pharmaceutically acceptable excipient.

Items A24. The process according to any one of items A14 to A23, wherein the at least one pharmaceutically acceptable excipient is selected from the group consisting of lactose, mannitol, microcrystalline cellulose, dicalcium phosphate, polyvinyl pyrrolidone, hydroxypropyl methylcellulose, croscarmellose sodium, crospovidone, sodium starch glycolate, colloidal silicon dioxide, magnesium stearate, sodium stearyl fumarate, or mixtures thereof.

Item A25. The process according to any one of items A14 to A24, wherein the final dosage form is encapsulated or tableted.

Item A26. A process for preparing a suspension comprising mixing the (b) mixture comprising 2-[(1R,3r,5S)-3-({5-cyclopropyl-3-[2-(trifluoromethoxy)phenyl]-1,2-oxazol-4-yl}methoxy-8-azabicyclo[3.2.1]octan-8-yl]-4-fluoro-1,3-benzothiazole-6-carboxylic acid, or a pharmaceutically acceptable salt thereof, and at least one binder, with water.

Item A27. A process for preparing a dispersible solution comprising mixing the (b) mixture comprising 2-[(1R,3r,5S)-3-({5-cyclopropyl-3-[2-(trifluoromethoxy) phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one binder, with an organic solvent.

Item A28. A solid dispersion comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole -6-carboxylic acid, or a pharmaceutically acceptable salt thereof, and at least one binder.

Item A29. A dispersible solution comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole -6-carboxylic acid, or a pharmaceutically acceptable salt thereof, and at least one binder, in an organic solvent.

Item A30. The pharmaceutical composition according to any one of items A1 to A13, for use as a medicine.

Item A31. The pharmaceutical composition according to any one of items A1 to A13, for use in the treatment of cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis, or liver fibrosis, preferably for primary biliary cirrhosis (PBS) or non-alcoholic steatohepatitis (NASH).

Item A32. Use of the pharmaceutical composition for oral administration as defined in items A1 to A13, for the manufacture of a medicament for cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis, or liver fibrosis, preferably for primary biliary cirrhosis (PBS) or non-alcoholic steatohepatitis (NASH).

Item A33. A pharmaceutical composition for oral administration comprising (a) an inert substrate, and (b) a mixture comprising 2-[(1R,3r,5S)-3-({5-cyclopropyl-3-[2-(trifluoromethoxy)phenyl]-1,2-oxazol-4-yl}methoxy)-8-aza bicyclo[3.2.1]octan-8-yl]-4-fluoro-1,3-benzothiazole -6-carboxylic acid, or a pharmaceutically acceptable salt thereof, and at least one binder.

Item A34. The pharmaceutical composition according to any one of items A1 to A13, and A33, wherein the inert substrate is present in an amount from about 16-fold w/w to about 6400-fold w/w, from about 100-fold w/w to about 3200-fold w/w, from about 400-fold w/w to about 1600-fold w/w, from about 800-fold w/w to about 1200-fold w/w, from about 900-fold w/w to about 1000-fold w/w based on an amount of the 2-[(1R,3r,5S)-3-({5-cyclopropyl-3-[2-(trifluoromethoxy)phenyl]-1,2-oxazol-4-yl}methoxy)-8-aza bicyclo[3.2.1]octan-8-yl]-4-fluoro-1,3-benzothiazole-6-carboxylic acid, or a pharmaceutically acceptable salt thereof.

Item A35. The pharmaceutical composition according to any one of items A1 to A13, A33, and A34, wherein the inert substrate is present in an amount about 100-fold w/w, about 300-fold w/w, about 500-fold w/w, about 600-fold w/w, about 700-fold w/w, about 800-fold w/w, about 900-fold w/w, about 1000-fold, about 1200-fold w/w, about 1500-fold w/w based on an amount of the 2-[(1R,3r,5S)-3-({5-cyclopropyl-3-[2-(trifluoromethoxy)phenyl]-1,2-oxazol-4-yl}methoxy)-8-aza bicyclo[3.2.1]octan-8-yl]-4-fluoro-1,3-benzothiazole-6-carboxylic acid, or a pharmaceutically acceptable salt thereof.

Item A36. The pharmaceutical composition according to any one of items A1 to A13, A33 to A35, wherein the at least one binder in the (b) mixture is present in an amount from about 0.5-fold w/w to about 300-fold w/w, from about 1-fold to about 150 fold w/w, from about 10-fold w/w to 100-fold w/w, from 25-fold w/w to about 75-fold w/w, or from about 40-fold w/w to about 60-fold w/w based on an amount of the 2-[(1R,3r,5S)-3-({5-cyclopropyl-3-[2-(trifluoromethoxy)phenyl]-1,2-oxazol-4-yl}methoxy)-8-aza bicyclo[3.2.1]octan-8-yl]-4-fluoro-1,3-benzothiazole-6-carboxylic acid, or a pharmaceutically acceptable salt thereof.

Item A37. The pharmaceutical composition according to any one of items A1 to A13, A33 to A36, wherein the binder is polyvinyl pyrrolidone.

Item A38. The pharmaceutical composition according to any one of items A1 to A13, A33 to A37, wherein the binder is present in an amount from about 10-fold w/w to about 100-fold w/w, or about 50-fold w/w based on an amount of the 2-[(1R,3r,5S)-3-({5-cyclopropyl-3-[2-(trifluoromethoxy)phenyl]-1,2-oxazol-4-yl}methoxy)-8-aza bicyclo[3.2.1]octan-8-yl]-4-fluoro-1,3-benzothiazole-6-carboxylic acid, or a pharmaceutically acceptable salt thereof.

Item A39. The pharmaceutical composition according to any one of items A1 to A13, A33 to A38, wherein 2-[(1R,3r,5S)-3-({5-cyclopropyl-3-[2-(trifluoromethoxy)phenyl]-1,2-oxazol-4-yl}methoxy)-8-aza bicyclo[3.2.1]octan-8-yl]-4-fluoro-1,3-benzothiazole-6-carboxylic acid, or a pharmaceutically acceptable salt thereof is present in an amount from about 0.05% w/w to about 2.5% w/w, from about 0.07% w/w to about 2% w/w, from about 0.08% w/w to about 1% w/w, from about 0.09% w/w to about 0.5% w/w, or from about 0.1% w/w to about 0.25% w/w relative to a weight of the pharmaceutical composition.

DETAILED DESCRIPTION OF THE INVENTION

The present invention provides Composition Comprising Compound A containing Compound A in low amounts. In one embodiment, Composition Comprising Compound A is directly processed into final dosage forms.

In another embodiment, at least one further active pharmaceutical ingredient Compound (B) is combined with Compound A in a dosage form. Compound (B) is introduced via Composition Comprising Compound B. Compound B can be a solid, or a liquid. Thus, Composition Comprising Compound B can be a particle, a granule, a dispersion (solid or liquid), a tablet, a mini-tablet, a bead, a pellet, a solution, or a mixture thereof. Composition Comprising Compound B can be combined with Composition Comprising Compound A to form Composition Comprising Compounds A and B which is then processed into final dosage forms.

Composition Comprising Compound A

The effective formulation of a low dose non-bile acid FXR agonist, such as 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, (Compound (A), as disclosed herein), proved difficult. For example, difficulties in weighing the low amount of non-bile acid FXR agonist, content uniformity, formulation, dissolution rate and bioavailability issues were observed. Ultimately, those issues were affecting the manufacturing process and in vivo performance of the pharmaceutical composition.

Surprisingly, it was found that those challenges can be overcome by preparing a pharmaceutical composition for oral administration comprising (a) an inert substrate, and (b) a mixture comprising a non-bile acid FXR agonist, and at least one binder. According to the present disclosure, the non-bile acid FXR agonist is 2-[(1R,3r,5S)-3-({5-cyclopropyl-3-[2-(trifluoromethoxy)phenyl]-1,2-oxazol-4-yl}methoxy)-8-azabicyclo [3.2.1]octan-8-yl]-4-fluoro-1,3-benzothiazole-6-carboxylic acid, or a pharmaceutically acceptable salt thereof (Compound (A)).

In one aspect, the pharmaceutical composition for oral administration of the present invention is a particle.

In one aspect the present invention provides a pharmaceutical composition for oral administration comprising particles, wherein said particles comprise (a) an inert substrate, and (b) a mixture comprising Compound (A) (2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof), and at least one binder.

According to the present invention, Compound (A) can also be present in its free form. The Compound (A), as described herein, may also be present in a crystalline form, in an amorphous form, or a mixture thereof.

In another aspect, the present invention also provides a pharmaceutical composition for oral administration comprising (a) an inert substrate, and (b) a mixture comprising a non-bile acid FXR agonist, and at least one binder. According to the present disclosure, the non-bile acid FXR agonist is 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof (Compound (A)).

According to the present invention, the pharmaceutical composition comprises an (a) inert substrate on which the (b) mixture comprising Compound (A), and at least one binder, is added. The (a) inert substrate comprises a material that does not chemically react to the (b) mixture comprising Compound (A), and at least one binder. The (a) inert substance is, for example, a pharmaceutically acceptable excipient known in the art not to interact chemically or physically with the active substance. Optionally, the (a) inert substrate can also be coated with a layer to protect the (a) inert substrate from any unwanted chemical or physical interaction that may happen during the formulation process. Optionally, the (a) inert substrate can also be treated with an acceptable excipient (for example, a binder) to render certain desirable process qualities, such as particle size and flowability, to the inert substance. The (a) inert substrate may comprise a material, which is selected from the group consisting of lactose, microcrystalline cellulose, mannitol, sucrose, starch, granulated hydrophilic fumed silica, tartaric acid, or mixtures thereof. Preferably, the material may comprise a material selected from the group consisting of lactose, microcrystalline cellulose, mannitol, sucrose, starch, granulated hydrophilic fumed silica, or mixtures thereof. More preferably, the material is lactose, or mannitol. The inert substrate can be present in an amount from about 16-fold w/w to about 6400-fold w/w, from about 100-fold w/w to about 3200-fold w/w, from about 400-fold w/w to about 1600-fold w/w, from about 800-fold w/w to about 1200-fold w/w, from about 900-fold w/w to about 1000-fold w/w based on the amount of Compound (A). In one embodiment, the inert substrate is present in an amount about 100-fold w/w, about 300-fold w/w, about 500-fold w/w, about 600-fold w/w, about 700-fold w/w, about 800-fold w/w, about 900-fold w/w, about 1000-fold, about 1200-fold w/w, about 1500-fold w/w based on the amount of Compound (A) or a pharmaceutically acceptable salt thereof.

Suitable binders for the (a) inert substance or the (b) mixture can be selected, for example, but not limited to, from the group consisting of cellulose acetate, cellulose fatty acid ester, cellulose nitrates (e.g. nitrocelluloses, nitrowools, Collodion), cellulose ether, ethyl cellulose, carboxymethyl cellulose (e.g. sodium cellulose gum, cellulose gum), methyl cellulose (e.g. cellulose methyl ether, Tylose), methylethyl cellulose, methylhydroxypropyl cellulose, polyvinyl pyrrolidone, hydroxypropyl cellulose, hypromellose (HPMC), hydroxyethyl cellulose, carboxyethyl cellulose, carboxymethyl hydroxyethyl cellulose, polyethylene glycol, polyvinyl alcohol, shellac, polyvinyl alcohol-polyethylene glycol co-polymer, or mixtures thereof. Preferably, the binder is selected from the group consisting of polyvinyl pyrrolidone, hydroxypropyl cellulose, hypromellose, carboxymethyl cellulose, methyl cellulose, hydroxyethyl cellulose, carboxyethyl cellulose, carboxymethyl hydroxyethyl cellulose, polyethylene glycol, polyvinylalcohol, shellac, polyvinyl alcohol-polyethylene glycol co-polymer, or mixtures thereof. More preferably, the binder is polyvinyl pyrrolidone (PVP).

The at least one binder present in the (b) mixture can be present in an amount from about 0.5-fold w/w to about 300-fold w/w, from about 1-fold to about 150 fold, from about 10-fold w/w to 100-fold w/w, from 25-fold w/w to about 75-fold w/w, or from about 40-fold w/w to about 60-fold w/w based on the amount of Compound (A), or a pharmaceutically acceptable salt thereof. The above-mentioned ranges apply for all the binders as listed above. Preferably, the binder is polyvinyl pyrrolidone. Preferably, the binder is present in an amount from about 10-fold w/w to about 100-fold w/w, from about 25-fold w/w to about 75-fold w/w, or from about 40-fold w/w to about 60-fold w/w based on the amount of Compound (A). More preferably, the binder is present in an amount about 50-fold w/w based on the amount of Compound (A), or a pharmaceutically acceptable salt thereof.

In accordance with the present invention, the (b) mixture comprising Compound (A), and at least one binder, can be added onto the (a) inert core using different techniques known in the art. For example, the (a) inert core can be sprayed or coated with the (b) mixture, using, for example, spray drying, spray layering, spray dispersing, spray coating, fluid bed drying, fluid bed coating, granulators with spray nozzles, or a combination of those spraying techniques thereof. Preferably, the (b) mixture comprising Compound (A), and at least one binder, is dispersed onto the (a) inert substrate. In another preferred aspect, the (a) inert substrate is coated with the (b) mixture comprising Compound (A), and at least one binder. The (b) mixture comprising Compound (A), and at least one binder, is preferably dispersed or coated onto the (a) inert core as discrete particles, thus, providing a large surface area for instant dissolution despite the poor solubility of the drug. As a result, a fast dissolution rate of Compound (A) can be achieved.

In accordance with the aspect of the present invention, the particle, as defined herein, optionally further comprises an outer (c) seal coating layer. The outer (c) seal coating layer comprises a material that does not chemically react with the (b) mixture comprising Compound (A), and at least one binder, and protects the (b) mixture, as defined herein, from any unwanted chemical or physical interaction that may happen during the formulation process, e.g. with additives, pharmaceutically acceptable excipients, or any further active pharmaceutical ingredient. The outer (c) seal coating layer also provides an additional barrier for taste masking. The outer (c) seal coating layer can also provide a barrier for gastric or stomach release while allowing for enteric or intestinal release. The outer (c) seal coating layer comprises, for example, hydroxypropyl methyl cellulose (HPMC), magnesium stearate, polyvinyl pyrrolidone, hydroxypropyl cellulose, carboxymethyl cellulose, methyl cellulose, hydroxyethyl cellulose, carboxyethyl cellulose, carboxymethylhydroxyethyl cellulose, polyethylene glycol, polyvinylalcohol, cellulose acetate phthalates (CAP), cellulose acetate trimellitates (CAT), hydroxypropyl methyl cellulose phthalates (HPMCP), hydroxypropyl methyl cellulose acetate succinate (HPMCAS), polyvinyl acetate phthalate (PVAP), methyl methacrylate-methacrylic acid copolymers, cellulose acetate succinate, fatty acids, waxes, shellac, sodium alginate, zein, or mixtures thereof. The outer (c) seal coating layer comprises, for example, hydroxypropyl methyl cellulose, magnesium stearate, polyvinyl pyrrolidone, hydroxypropyl cellulose, carboxymethyl cellulose, methyl cellulose, hydroxyethyl cellulose, carboxyethyl cellulose, carboxymethylhydroxyethyl cellulose, polyethylene glycol, polyvinylalcohol, or mixtures thereof. Preferably, the outer (c) seal coating layer comprises magnesium stearate, hydroxypropyl methyl cellulose, or mixtures thereof. More preferably, the material used for the outer (c) seal coating layer is hydroxypropyl methyl cellulose (HPMC).

The material used for the outer (c) seal coating layer can be present in an amount of about 0.5% w/w to about 6% w/w based on the total weight of the particles. Preferably, in an amount of 1% w/w to about 5% w/w based on the total weight of the particles. More preferably, in an amount of about 3% w/w based on the total weight of the particles. The above-mentioned ranges apply to all outer (c) seal coating layer materials as listed above.

According to the present invention, the size of the particle corresponds to the size of the (a) inert substrate, as disclosed herein, together with the coating. For example, the particle can have a size from about 20 μm to about 500 μm. Preferably, the particle can have a size from about 50 μm to 400 μm. More preferably, the particle can have a size of about 100 μm to about 300 μm. The particle size is measured, for example, by laser diffraction methodology (e.g. particle size distribution (PSD)). For example, the particle size is measured using the instrument and method disclosed herein.

A further aspect of the present invention provides a process for preparing the pharmaceutical composition for oral administration, said process comprising the steps of:

(i) Mixing the (b) mixture comprising Compound (A) (2-[(1R,3r,5S)-3-({5-cyclopropyl -3-[2-(trifluoromethoxy)phenyl]-1,2-oxazol-4-yl}methoxy)-8-azabicyclo[3.2.1]octan-8-yl]-4-fluoro -1,3-benzothiazole-6-carboxylic acid, or a pharmaceutically acceptable salt thereof), with at least one binder, as defined herein, and optionally with at least one polar protic solvent, as defined herein; and (ii) Adding said mixture (i) to the (a) inert substrate, as defined herein.

A further aspect of the present invention provides a process for preparing the pharmaceutical composition for oral administration, said process comprising the steps of:

(i) Mixing the (b) mixture comprising Compound (A) (2-[(1R,3r,5S)-3-({5-cyclopropyl -3-[2-(trifluoromethoxy) phenyl]-1,2-oxazol-4-yl}methoxy)-8-azabicyclo[3.2.1]octan-8-yl]-4-fluoro -1,3-benzothiazole-6-carboxylic acid, or a pharmaceutically acceptable salt thereof), with at least one binder, as defined herein, and optionally with at least one polar protic solvent, as defined herein; and (ii) Adding said mixture (i) to the (a) inert substrate, as defined herein, wherein said polar protic solvent, when present, is removed at a temperature of about 20° C. to about 130° C. Preferably, the polar protic solvent is removed at a temperature of about 50° C. to about 110° C. More preferably, at a temperature of about 70° C. to about 100° C.

A further aspect of the present invention provides a process for preparing the pharmaceutical composition for oral administration comprising particles, as defined herein, said process comprising the steps of:

(i) Mixing the (b) mixture comprising Compound (A) (2-[(1R,3r,5S)-3-({5-cyclopropyl -3-[2-(trifluoromethoxy) phenyl]-1,2-oxazol-4-yl}methoxy)-8-azabicyclo[3.2.1]octan-8-yl]-4-fluoro -1,3-benzothiazole-6-carboxylic acid, or a pharmaceutically acceptable salt thereof), with at least one binder, as defined herein, and optionally with at least one polar protic solvent, as defined herein; and (ii) Adding said mixture (i) to the (a) inert substrate of the particles, as defined herein.

The pharmaceutical composition can comprise particles comprising Compound (A), wherein compound (A) is present from about 0.05% w/w to about 2.5% w/w, from about 0.07% w/w to about 2% w/w, from about 0.08% w/w to about 1% w/w, from about 0.09% w/w to about 0.5% w/w, or from about 0.1% w/w to about 0.25% w/w of Compound (A) relative to the total dry weight of the pharmaceutical composition. For example, at about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.20%, about 0.3%, about 0.5%, about 1%, about 1.5%, about 2%, or about 2.5% w/w relative to the total dry weight of the composition. Preferably, compound (A) is present from about 0.05% to about 0.25%, or from about 0.08% to about 0.15% w/w relative to the total dry weight of the pharmaceutical composition.

The at least one protic polar solvent comprises organic solvents, water, or mixtures thereof. Suitable, protic polar organic solvents can be selected from, for example, but not limited to, methanol, ethanol, isopropanol, n-propanol, n-butanol, sec-butanol, iso-butanol, tert-butanol, hexanol, nitromethane, or mixtures thereof. Preferably, the organic solvent is selected from the group consisting of methanol, ethanol, isopropanol, n-propanol, n-butanol, or mixtures thereof. More preferably, the protic polar solvent is water, ethanol, or mixtures thereof. Particularly, the organic solvent is ethanol. The optionally at least one polar protic solvent is evaporated at a temperature of about 20° C. to about 130° C. Preferably, the at least one polar protic solvent is removed at a temperature of about 50° C. to about 110° C. More preferably, at a temperature of about 70° C. to about 100° C.

Another aspect of the present invention relates to a process for preparing the pharmaceutical composition for oral administration comprising particles, as defined herein, said process comprising the steps of:

(i) Mixing the (b) mixture comprising Compound (A) (2-[(1R,3r,5S)-3-({5-cyclopropyl -3-[2-(trifluoromethoxy) phenyl]-1,2-oxazol-4-yl}methoxy)-8-azabicyclo[3.2.1]octan-8-yl]-4-fluoro -1,3-benzothiazole-6-carboxylic acid, or a pharmaceutically acceptable salt thereof), with at least one binder, as defined herein, and optionally with at least one polar protic solvent, as defined herein; and (ii) Adding said mixture (i) to the (a) inert substrate of the particles, as defined herein; wherein said polar protic solvent, when present, is removed at a temperature of about 20° C. to about 130° C. Preferably, the polar protic solvent is removed at a temperature of about 50° C. to about 110° C. More preferably, at a temperature of about 70° C. to about 100° C. Another aspect of the present invention relates to a process for preparing the pharmaceutical composition for oral administration comprising particles, as defined herein, said process comprising the steps of:

(i) Mixing the (b) mixture comprising Compound (A) (2-[(1R,3r,5S)-3-({5-cyclopropyl -3-[2-(trifluoromethoxy) phenyl]-1,2-oxazol-4-yl}methoxy)-8-azabicyclo[3.2.1]octan-8-yl]-4-fluoro -1,3-benzothiazole-6-carboxylic acid, or a pharmaceutically acceptable salt thereof), with at least one binder, as defined herein, in the presence of an organic solvent, water, or mixture thereof, as defined herein; and (ii) Adding said mixture (i) to the (a) inert substrate of the particles, as defined herein.

Another aspect of the present invention relates to a process for preparing the pharmaceutical composition for oral administration, as defined herein, wherein the mixture of step (i) is dispersed onto the (a) inert substrate.

Yet another aspect of the present invention relates to a process for preparing the pharmaceutical composition for oral administration, as defined herein, wherein the (a) inert substrate is coated with the mixture of step (i).

A further aspect of the present invention relates to a process for preparing the pharmaceutical composition for oral administration, as defined herein, said process further comprising the step of adding an outer (c) seal coating layer onto said particles.

The (c) seal coating layer, as defined herein, prevents chemical-physical interactions between the particles and any other active or non-active substances that may be used in the preparation of the final dosage form.

Another aspect of the present invention relates to the process for preparing the pharmaceutical composition for oral administration comprising particles, as defined herein, said process comprising, for example, the steps of:

(i) Mixing the (b) mixture comprising Compound (A), with at least one binder, preferably the binder is polyvinyl pyrrolidone, in the presence of ethanol, to obtain a solution;

(ii) Adding the solution from step (i) to the (a) inert substrate of the particles, preferably, the (a) inert substrate is lactose or mannitol; and (iii) Optionally adding an outer (c) seal coating layer onto said particles, preferably, the (c) seal coating layer is hypromellose (HPMC).

Another aspect the present invention provides for a process for preparing a dispersible solution comprising mixing the (b) mixture comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole -6-carboxylic acid, or a pharmaceutically acceptable salt thereof, and at least one binder with an organic solvent, as defined herein. Preferably, the organic solvent is ethanol.

Another aspect the present invention relates to a dispersible solution comprising 2-[(1R,3r,5S)-3-({5-cyclopropyl-3-[2-(trifluoromethoxy)phenyl]-1,2-oxazol-4-yl}methoxy)-8-azabicyclo [3.2.1]octan-8-yl]-4-fluoro-1,3-benzothiazole-6-carboxylic acid, or a pharmaceutically acceptable salt thereof, and at least one binder, in an organic solvent.

Another aspect of the present invention relates to the process for preparing the pharmaceutical composition for oral administration comprising particles, as defined herein, said process comprising, for example, the steps of:
(i) Mixing the (b) mixture comprising Compound (A), with at least one binder, preferably the binder is polyvinyl pyrrolidone, in the presence of water, to obtain a suspension;
(ii) Adding the suspension from step (i) to the (a) inert substrate of the particles, preferably, the (a) inert substrate comprises a material which is selected from the group consisting of lactose, microcrystalline cellulose, mannitol, sucrose, starch, granulated hydrophilic fumed silica, or mixtures thereof; and
(iii) Optionally adding an outer (c) seal coated layer onto said particles, preferably, and the (c) seal coated layer is hypromellose (HPMC).

Another aspect of the present invention provides for a process for preparing a suspension comprising mixing the (b) mixture comprising 2-[(1R,3r,5S)-3-({5-cyclopropyl-3-[2-(trifluoromethoxy)phenyl]-1,2-oxazol-4-yl}methoxy-8-azabicyclo[3.2.1]octan-8-yl]-4-fluoro-1,3-benzothiazole-6-carboxylic acid, or a pharmaceutically acceptable salt thereof, at least one binder, with water, as defined herein.

Another aspect of the present invention relates to a solid dispersion comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one binder, in water, as defined herein.

Another aspect of the present invention also provides for a process, as defined herein, comprising the step of further adding at least one additional active pharmaceutical ingredient.

Another aspect of the present invention provides for a process further comprising preparing the final dosage form by mixing the particles with at least one pharmaceutically acceptable excipient. The at least one pharmaceutically acceptable excipient can be selected, for example, from the group consisting of lactose, mannitol, microcrystalline cellulose, dicalcium phosphate, polyvinyl pyrrolidone, hydroxypropyl methylcellulose, croscarmellose sodium, crospovidone, sodium starch glycolate, colloidal silicon dioxide, magnesium stearate, sodium stearyl fumarate, or mixtures thereof. Preferably, the excipient can be selected from the group consisting of mannitol, croscarmellose sodium, colloidal silicon dioxide, magnesium stearate, or mixtures thereof.

The pharmaceutical composition comprising Compound A either with or without a binder, an inert substrate, or other excipients is hereafter referred to as Composition Comprising Compound A. In one embodiment, compound (A) or a pharmaceutically acceptable salt thereof is present from about 0.05% to about 2.5%, from about 0.07% to about 2%, from about 0.08% to about 1%, from about 0.09% to about 0.5%, or from about 0.1% to about 0.25% w/w relative to the total weight of Particles Comprising Compound A. For example, at about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.20%, about 0.3%, about 0.5%, about 1%, about 1.5%, about 2%, or about 2.5% w/w relative to the total eight of Particles Comprising Compound A. Preferably, compound (A) or a pharmaceutically acceptable salt thereof is present from about 0.05% to about 0.25%, or from about 0.08% to about 0.15% w/w relative to the total weight of Composition Comprising Compound A.

Composition Comprising Compound B

The present disclosure provides a composition, such as a solid composition, comprising Compound B. The identity of Compound B is not particularly limited. In some instances, Compound B itself is a combination of two or more active pharmaceutical ingredients. Compound B can be a solid or a liquid. Thus, Composition Comprising Compound B can be a particle, a granule, a dispersion (solid or liquid), a tablet, a mini-tablet, a bead, a pellet, a solution, or a mixture thereof.

Compound B may be selected from the following classes of active pharmaceutical ingredients: glucagon-like peptide 1 (GLP-1) receptor agonists (GLP-1RAs), dipeptidyl peptidase-4 (DPP4) inhibitors, peroxisome proliferator-activated receptor (PPARs) agonists, acetyl-CoA carboxylase (ACC) inhibitors, thyroid hormone receptor β (TRβ) agonists, ketohexokinase (KHK) inhibitors, diacylglycerol Acyltransferase 2 (DGAT2) inhibitors, sodium-glucose linked transporter (SGLT) inhibitors, anti-inflammatory agents (such as chemokine receptor 2/5 (CCR2/5) antagonists), and anti-fibrosis agents (such as Galectin-3 inhibitors and Lysyl oxidase-like 2 (LOXL 2) inhibitors).

In addition to Compound B, the composition can have one or more additional ingredients, for example one or more binders, one or more fillers, one or more disintegrants, or one or more lubricants. Further additional ingredients can also be present, although it should be understood that no particular additional ingredient is required.

The one or more binders are discussed in the context of Composition Comprising Compound A above.

The one or more fillers, when used, can include at least one of lactose, microcrystalline cellulose, calcium phosphate dibasic anhydrous,calcium phosphate dibasic dihydrate, calcium phosphate tribasic, cellulose powder, magnesium carbonate, calcium sulfate, starch, talc, sucrose, dextrose, mannitol, hydroxypropylmethyl cellulose, hydroxypropyl cellulose, carboxymethylcellulose, fructose, xylitol, sorbitol, and combinations thereof.

The one or more disintegrants, when used, can include at least one of cross-linked polyvinylpyrrolidone, cross-linked sodium carboxymethyl cellulose, and sodium starch glycolate. For example, the one or more disintegrants can be cross-linked sodium carboxymethyl cellulose. The weight ratio of the one or more disintegrants, such as cross-linked sodium carboxymethyl cellulose, to Compound B is not particularly limited. For example, the one or more disintegrants can be present in an amount of from about 2% to about 10%, such as about 4% to about 8%, or about 6%, by weight of the composition.

The one or more lubricants, when used, can include at least one of talc, silica, stearin, magnesium stearate, or stearic acid. For example, the one or more lubricants can be magnesium stearate. The one or more lubricants can be present in an amount of from about 0.25% to about 5%, such as from about 0.75% to about 3%, or about 1.25%, by weight of the composition.

Further additional ingredients that can be used are listed in Remington: The Science and Practice of Pharmacy, which is hereby incorporated by reference in its entirety for all purposes.

The composition discussed above containing Compound B is referred to as Composition Comprising Compound B (containing Compound B with or without other excipients) hereafter.

Composition Comprising Compounds A and B

The current invention also provides a fixed dose combination containing Compounds A and B. As discussed above, the effective formulation of low doses of Compound A or a pharmaceutically acceptable salt thereof proved difficult. The current invention overcomes the difficulties in formulating a fixed dose combination composition containing both Compounds A and B by utilizing each of Composition Comprising Compound A and Composition Comprising Compound B as intermediates. The fixed dose combination composition prior to the conversion to a final dosage form is referred to as Composition Comprising Compounds A and B hereafter.

The current invention provides compatible Composition Comprising Compound A and Composition Comprising Compound B. The free combination of the two allows Compound A and Compound B in a desired proportion according to the desired pharmaceutical and/or therapeutic effects. The The compatibility allows ready preparation of unit dosage forms, or multiple-dosage forms from Composition Comprising Compounds A and B.

As an example, Composition Comprising Compound A and Composition Comprising Compound B are combined (e.g. mixed or blended) in a proportion for a desired therapeutic effect. One or more of the binders, fillers, disintegrants, lubricants, and other additional ingredients discussed above can also be admixed in the combining process. The method of combining is not particularly limited.

Dosage Forms

The pharmaceutical composition comprising Composition Comprising Compound (A) may be directly converted into final dosage forms. Alternatively, as discussed above in detail, Composition Comprising Compound (A) may also be combined with Composition Comprising Compound B to form Composition Comprising Compounds A and B which then is processed into final dosage forms.

Another aspect the present invention provides for a process, as defined herein, wherein the final dosage form is encapsulated or tableted.

The pharmaceutical composition, as disclosed herein, is intended to be administered orally to humans and animals in unit dosage forms, or multiple-dosage forms, such as, for example, a capsule, a caplet, a powder, pellets, granules, a tablet, a mini-tablet, a sachet, a pouch, or a stick pack. The pharmaceutical composition may contain Compound (A) or also with Compound (B) as described above. Preferably, the unit dosage form, or multi-dosage form, for example, is a capsule, a tablet, a mini-tablet, a sachet, a pouch, or a stick pack. More preferably, the pharmaceutical composition is in the form of a capsule, or a tablet. This can be achieved by mixing the pharmaceutical composition, as defined herein, with diluents, lubricants, binders, disintegrants, and/or absorbents, colorants, flavours and sweeteners.

Capsules comprising the particles or the compositions of the invention, as defined herein, can be prepared using techniques known in the art. Suitable capsules can be selected from a soft gelatin capsule, a hard shell capsule, a hard gelatin capsule, a plant-based shell capsule, a hypromellose (HPMC) based capsule, or mixtures thereof.

The pharmaceutical composition, as described herein, can be presented in a hard gelatin capsule, a soft gelatin capsule, a hard shell capsule, or a hard plant shell capsule, hypromellose (HPMC) capsule wherein the pharmaceutical composition is further mixed with an inert solid diluent, for example, calcium carbonate, calcium phosphate, or cellulose-based excipient. The hard gelatin capsules are made of two-piece outer gelatin shells referred to as the body and the cap. The shell may comprise vegetal or animal gelatin (e.g. pork, beef, or fish based gelatin), water, one or more plasticizers, and possibly some preservatives. The capsule may hold a dry mixture, in the form of a powder, very small pellets, or particles, comprising a non-bile acid FXR agonist, such as Compound (A), at least one binder, and optionally excipients. The shell may be transparent, opaque, coloured, or flavoured. The capsules containing the particles can be coated by techniques well known in the art with enteric- and/or gastric-resistant or delayed-release coating materials, to achieve, for example, greater stability in the gastrointestinal tract, or to achieve the desired rate of release. Hard gelatin capsules of any size (e.g. size 000 to 5) can be prepared.

Tablet comprising the particles of the invention, as defined herein, can be prepared using techniques known in the art. Suitable tablets may contain the particles in admixture with non-toxic pharmaceutical, which are suitable for the manufacture of tablets. These excipients are, for example, inert diluents, such as calcium carbonate, sodium carbonate, lactose (e.g. lactose SD), mannitol (e.g. mannitol DC), magnesium carbonate, kaolin, cellulose (e.g. microcrystalline cellulose, powdered cellulose), calcium phosphate, or sodium phosphate; granulating and disintegrating agents, for example, croscarmellose sodium, crospovidone, sodium starch glycolate, corn starch, or alginic acid; gliding agents, for example, fumed silica (e.g. Aerosil®, Aeroperl®); binding agents (e.g. for example, methyl cellulose, carboxymethyl cellulose, polyvinyl pyrrolidone, starch, gelatin, or acacia); and lubricating agents, for example magnesium stearate, sodium stearyl fumarate, stearic acid or talc. The mixture of the particles in admixture with non-toxic pharmaceutical can be mixed using numerous known methods, such as, for example, mixing in a free-ball, or tumble blending. The mixture of the particles in admixture with non-toxic pharmaceutical can be compressed into a tablet using tableting techniques known in the art, such as, for example, a single punch press, a double punch press, a rotary tablet press, or a compaction on a roller compaction equipment. The compression force applied to form the tablet can be any suitable compression force that allows obtaining a tablet, for example, the compression applied can be between 0.5 to 50 kN, preferably between 1 to 30 kN. The tablets can be uncoated or coated by known techniques to delay disintegration and absorption in the gastrointestinal tract and thereby provide a sustained action over a longer period. For example, tablets can be coated with a suitable polymer or a conventional coating material to achieve, for example, greater stability in the gastrointestinal tract, or to achieve the desired rate of release, for example the tablet can be coated with hypromellose (HPMC), magnesium stearate, polyethylene glycol (PEG), polyvinyl alcohol (PVA), Opadry®, Opadry II®, or mixtures thereof. For example, a time delay material such as glyceryl monostearate or glyceryl distearate can be employed. Tablets of any shape or size can be prepared, and they can be opaque, coloured, or flavoured.

A flow chart depicting the manufacturing process of the pharmaceutical composition comprising Compound (A) is shown in FIG. A.

The inert substrate, such as lactose or mannitol, may be pre-treated to provide a granule so that the particle size is in an acceptable range, for example. The pre-treatment may employ an adequate binder, for example, HPMC and polyvinylpyrrolidone. The pre-treatment granulation can be a dry or wet process. The API such as Compound A is then layered onto the pre-treated inert substrate as described above.

The non-bile acid FXR agonist, such as Compound (A), alone or in combination with a second active pharmaceutical ingredient, as disclosed herein, are present in the pharmaceutical composition in an amount sufficient to exert a therapeutically useful effect in the absence of undesirable side effects on the patient treated. Due to the high potency of Compound (A), a low dose is preferable. Each unit dose contains a predetermined amount of the Compound (A), sufficient to produce the desired therapeutic effect. Each unit dose as disclosed herein, are suitable for human and animal subjects, are packaged individually and may be administered in fractions or multiples thereof. A multiple-dose form is a plurality of identical unit-dosage forms packaged in a single container to be administered in segregated unit-dose form. Examples of multiple-dose forms include vials, blisters, or bottles.

In accordance with the present invention, Compound (A) or its pharmaceutically acceptable salt may be present in the pharmaceutical composition for oral administration in a low amount. In one aspect of the present invention relates to a pharmaceutical composition for oral administration wherein the final dosage form comprises Compound (A) or its pharmaceutically acceptable salt, in an amount of about 0.01 mg to about 2 mg, about 0.03 mg to about 1.5 mg, about 0.05 mg to about 1 mg, or about 0.07 mg to about 0.09 mg. Preferably, the low amount of the non-bile acid FXR agonist, such as Compound (A), is about 0.01 mg, or about 0.02 mg, or about 0.03 mg, or about 0.04 mg, or about 0.05 mg, or about 0.06 mg, or about 0.07 mg, or about 0.08 mg, or about 0.09 mg, or about 0.1 mg, or about 0.12 mg, or about 0.14 mg, or about 0.15 mg, or about 0.2 mg, or about 0.25 mg, or about 0.5 mg, or about 0.8 mg, or about 1 mg, or about 1.2 mg, or about 1.4 mg, or about 1.5 mg, or about 1.8 mg, or about 2 mg. More particularly, the amount is about 0.01 mg, or is about 0.03 mg, or is about 0.09 mg, or is about 0.1 mg, or is about 0.12 mg, or is about 0.14 mg, or is about 0.25 mg, or is about 0.5 mg, or is about 1 mg, or is about 1.5 mg, or the amount is about 2 mg. More preferably, the amount is about 0.01 mg, or is about 0.03 mg, or is about 0.09 mg, or is about 0.1 mg, or is about 0.5 mg, or the amount is about 2 mg.

A further aspect of the invention relates to a pharmaceutical composition for oral administration, as defined herein, comprising at least one further active pharmaceutical ingredient Compound (B) in a therapeutically effective amount.

Use

The pharmaceutical composition for oral administration, as disclosed herein, is useful, for example, as medicine, for the treatment of an FXR mediated condition or disorder such as, for example, cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis, or liver fibrosis. Specifically, the present disclosure provides the use of said pharmaceutical composition in the treatment of primary biliary cirrhosis (PBS), or non-alcoholic steatohepatitis (NASH).

Accordingly, the final dosage form for oral administration, prepared from the pharmaceutical composition of the current invention, is useful, for example, as medicine, for the treatment of an FXR mediated condition or disorder such as, for example, cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis, or liver fibrosis. Specifically, the present disclosure provides the use of said pharmaceutical composition in the treatment of primary biliary cirrhosis (PBS), or non-alcoholic steatohepatitis (NASH).

Another aspect of the invention also provides for the use of the pharmaceutical composition, as disclosed herein, for the manufacture of a medicament for cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis, or liver fibrosis, preferably for primary biliary cirrhosis (PBS), or non-alcoholic steatohepatitis (NASH). Specifically, the present disclosure provides the use of said pharmaceutical composition in the treatment of primary biliary cirrhosis (PBS), or non-alcoholic steatohepatitis (NASH).

Another aspect of the invention also provides for a method of treating a disease or disorder in a patient in need thereof, wherein the disease or disorder is cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis, or liver fibrosis, comprising the step of administering to the patient an effective amount of the pharmaceutical composition or the final dosage form. Specifically, the present disclosure provides a method of treating primary biliary cirrhosis (PBS), or non-alcoholic steatohepatitis (NASH).

DEFINITIONS

The term "farnesoid X receptor" or "FXR" refers to all mammalian forms of such receptors including, for example, alternative splice isoforms and naturally occurring isoforms (Huber et al. *Gene,* 2002, 290, 35). Representative farsenoid X receptor species include, without limitation, the rat (GenBank Accession No. NM_021745), the mouse (GenBank Accession No. NM_009108), and the human (GenBank Accession No. NM_005123) forms of the receptor.

The term "non-bile acid FXR agonist" refers to an agent that directly binds to and upregulates the activity of non-bile acid FXRs. Particularly, the term "agonist" refers to an agent that triggers at least one response by binding a non-endogenous ligand to the receptor. The agonist may act directly or indirectly with a second agent that itself modulates the activity of the receptor. The agonist may also act indirectly by modulating the activity of one or more agent(s) that modulate the amount of FXR mRNA or FXR protein in certain cells of a patient.

The term "pharmaceutically acceptable salts" refers to salts that can be formed, for example, as acid addition salts, preferably with organic or inorganic acids. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. The term "pharmaceutically acceptable" refers to those compounds, materials, compositions, and/or dosage forms which are suitable for use in contact with the tissues of human beings and animals without excessive toxicity, irritation, allergic response, other problem or complication, commensurate with a reasonable benefit/risk ratio.

The term "treat", treating" or "treatment" of any disease or disorder refers to ameliorating the disease or disorder (e.g. slowing, arresting or reducing the development of the disease, or at least one of the clinical symptoms thereof), to preventing, or delaying the onset, or development, or progression of the disease or disorder. In addition those terms refer to alleviating or ameliorating at least one physical parameter including those which may not be discernible by the patient and also to modulating the disease or disorder, either physically (e.g. stabilization of a discernible symptom), physiologically (e.g. stabilization of a physical parameter), or both.

The term "about", as used herein, is intended to provide flexibility to a numerical range endpoint, providing that a given value may be "a little above" or "a little below" the endpoint accounting for variations one might see in the measurements taken among different instruments, samples, and sample preparations. The term usually means within 10%, preferably within 5%, and more preferably within 1% of a given value or range.

The terms "pharmaceutical composition" or "formulation" can be used herein interchangeably, and relate to a physical mixture containing a therapeutic compound to be administered to a mammal, e.g. a human, in order to prevent, treat, or control a particular disease or condition affecting a mammal. The terms also encompass, for example, an intimate physical mixture formed at high temperature and pressure.

The term "oral administration" represents any method of administration in which a therapeutic compound can be administered through the oral route by swallowing, chewing, or sucking an oral dosage form. Such oral dosage forms are traditionally intended to substantially release and/or deliver the active agent in the gastrointestinal tract beyond the mouth and/or buccal cavity.

The term "a therapeutically effective amount" of a compound, as used herein, refers to an amount that will elicit the biological or medical response of a subject, for example, ameliorate symptoms, alleviate conditions, slow or delay disease progression, etc. The term "a therapeutically effective amount" also refers to an amount of the compound that, when administered to a subject, is effective to at least partially alleviate and/or ameliorate a condition, a disorder, or a disease. The term "effective amount" means the amount of the subject compound that will engender a biological or medical response in a cell, tissue, organs, system, animal or human that is being sought by the researcher, medical doctor or other clinician.

The term "comprising" is used herein in its open ended and non-limiting sense unless otherwise noted. In a more limited embodiment "comprising" can be replaced by "consisting of", which is no longer open-ended. In a most limited version it can include only feature steps, or values as listed in the respective embodiment.

The terms "low dose", "low dosage strength", or "low amount", as used herein, can be used interchangeably, and refer to a low amount of the active pharmaceutical ingredient ranging from about 0.001 mg to about 10 mg, preferably to an amount ranging from about 0.1 mg to about 2 mg.

The term "particle(s)", as used herein, refers to a particle or particles, comprising an (a) inert substrate, and (b) a mixture comprising compound (A), and at least one binder. The inert substrate, as disclosed herein, together with the coating defines the size of the particle. For example, the particle can have a size from about 20 µm to about 500 µm. Preferably, the particle can have a size from about 50 µm to 400 µm. More preferably, the particle can have a size of about 100 µm to about 300 µm. The particle size is measured, for example, by by laser diffraction methodology (e.g. particle size distribution (PSD)), using the equipment described herein.

The term "inert substrate", as used herein, refers to a substance or a material that does not react with neither a chemically or biologically reactive substance, and will not decompose.

The term "binder", is used herein in its established meaning in the field of pharmaceutics. It refers to a non-active substance that is added alongside the active pharmaceutical ingredient (herein referred to as Compound (A)), e.g. adhesion to the inert substrate particles in case of compound (A) deposition or in case of tableting as a promoter of cohesive compacts which enables to form granules and which ensures that granules can be formed with the required mechanical strength. All binders, referred herein, are used in qualities suitable for pharmaceutical use and are commercially available under various brand names as indicated in the following examples:

Polyvinyl pyrrolidone (INN Ph. Eur.) is commercially available under the trade name Povidone K30 or PVP K30 (approximate molecular weight 50 000).

Shellac (INN Ph. Eur.) is a commercially available resin excreted by the females of the insects *Laccifer lacca* Kerr, *Kerria Lacca* Kerr, *Tachardia lacca, Coccus lacca* and *Carteria lacca* on various trees. Shellac composition is as follows: 46% Aleuritic acid ($HOCH_2(CH_2)_5CHOHCHOH(CH_2)_7COOH$), 27% Shellolic acid (a cyclic dihydroxy dicarboxylic acid and its homologues), 5% Kerrolic acid ($CH_3(CH_2)_{10}(CHOH)_4COOH$), 1% Butolic acid ($C_{14}H_{28}(OH)(COOH)$), 2% Esters of wax alcohols and acids, 7% Non-identified neutral substances (e.g. coloring substances, etc), and 12% Non-identified polybasic esters.

Polyvinyl alcohol (INN Ph. Eur.) is commercially available under the trade name Polyviol or PVA (approximate molecular weight 28 000 to 40 000).

Polyethylene glycol (Ph. Eur.) is commercially available under the trade name PEG-n, where "n" is the number of ethylene oxide units (EO-units) (approximate molecular weight up to 20 000).

Polyvinyl alcohol-polyethylene glycol co-polymer also known as polyvinyl alcohol-PEG copolymer.

The molecular weight throughout the specification is in the unit of Dalton.

ABBREVIATIONS

% w/w Percent weight by weight
ALT alanine aminotransferase
API Active pharmaceutical ingredient
AV Acceptance value
BMI Body mass index
C4 7-hydroxy-4-cholesten-3-one
CAP Cellulose acetate phthalates CAT Cellulose acetate trimellitates
CU Content uniformity
DAD Diode array detector
DSC Differential Scanning calorimetry
FGF fibroblast growth factor
FXR Farsenoid X receptor
g/min Gram per minute
GGT gamma-glutamyl transferase
HCl Hydrochloric acid
HDL-C High-density lipoprotein cholesterol
HPMC Hypromellose/hydroxypropylmethyl cellulose
HPMCAS Hydroxypropyl methyl cellulose phthalates
INCI International Nomenclature of Cosmetic Ingredients
INN International nonproprietary name
Kg/g/mg/ng/pg Kilogram/Gram/Milligram/Nanogram/Microgram
kN Kilo Newton
LC (%) Percent of label claim
LDL-C low-density lipoprotein cholesterol
LFC liver fat content
LOS Loss on drying
m³/h Cubic meter per hour
mbar millibar
mL/L Milliliters/Liters
MRI-PDFF magnetic resonance imaging-proton density fat fraction
N Normal
NAFLD Non-alcoholic fatty liver disease
NASH Non-alcoholic steatohepatitis
° C. Degree Celsius
PBC Primary biliary cirrhosis
PEG Polyethylene glycol
Ph. Eur. European Pharmacopoeia (9$^{th}$ edition)
PSD Particle Size Distribution
PVA Polyvinyl alcohol
PVAP Polyvinyl acetate phthalate
Q(%) Amount of active released
Q.S Quantity sufficient
RH Relative humidity
RSD Relative standard deviation
Sec/msec Seconds/milliseconds
SEM Scanning Electron Microscopy
TFA Trifluoroacetic acid
TG triglycerides
USP United States Pharmacoepia
UV Ultra Violet
w/v weight by volume
w/w weight by weight
XRPD X-ray Powder Diffraction

EXAMPLES

The following examples illustrate the invention and provide support for the disclosure of the present invention without limiting the scope of the invention.

Analytical Details

Dissolution conditions: The dissolution analysis were performed using a USP II (paddles) apparatus in a medium comprising 0.5% w/v sodium lauryl sulfate in 0.1 N HCl, at a temperature of 37.0±0.5° C. Analysis were performed in a 900 ml vessel or in a 500 ml vessel.

Assay and degradation: The analysis was performed using the following

Column: Agilent pursuit XRs 3µm C18 150×3mm, column temperature 30° C.

Detection: UV or DAD

Gradient: Eluant A: 0.05% TFA in water/Eluant B: 0.05% acetonitrile

| Time [min] | % A (Eluent A) | % B (Eluent B) |
|---|---|---|
| 0.0 | 86 | 14 |
| 15.3 | 14 | 86 |
| 20.4 | 14 | 86 |
| 20.5 | 0 | 100 |
| 24.0 | 0 | 100 |
| 24.1 | 86 | 14 |
| 30.0 | 86 | 14 |

Content uniformity: The content uniformity analysis was performed using the following:

Column: Kinetex XB-C18% 5 µm 150×4.6, column temperature 30° C.

Detection: UV or DAD

Eluant A: 0.05% TFA in water/Eluant B: 0.05% acetonitrile (no gradient).

XRPD: The X-Ray Powder Diffraction (XRPD) analysis was performed using a Panalytical Xpert Pro diffractometer equipped with a Cu X-ray tube and a Pixcel detector system, using a monochromatic Cu(Kα)-radiation. About 20 mg of each material was analyzed at ambient temperature in transmission mode held between low density polyethylene films. The Instrument parameters are as follows:

Sample prep Transmission foil
Range: 3-40°2 θ degrees
Step size: 0.013°
Counting time: (Step time)~90 s
Run time: 20min

| Incident Optics | Soller slits: 0.02 rad |
| | Mirror: Beam Cu W/Si focusing MPD |
| | Divergence slit: ½° |
| | Antiscatter slit: ½° |
| | NO Beam attenuator, Mask or Filter |
| Diffracted Optics | Detector: PIXcel |
| | Soller slits: Large 0.02 rad |
| | Antiscatter slit: AS slit 7.5 mm Pixcel |

DSC: Differential Scanning calorimetry (DSC) analysis was carried out using a Perkin Elmer Jade DSC system. The sample was weighed into an aluminum pan and a lid was crimped into position. The sample was heated under a nitrogen environment from about 30° C. to 300° C. using a heating rate of 10° C./minute.

PSD: Particle size distribution was determined using the Malvern Mastersizer 3000 (MS3000) equipped with an Aero S dry dispersion unit and micro tray. The Instrument parameters are as follows:

Lens/measuring range: 0.01 µm-3500 µm
Analysis sensitivity: Normal
Calculation model: Mie (material refractive index: 1.540, absorption: 0.01)
Particle type: Non-spherical mode
Obscuration filtering: Yes_Obscuration limits: 0.10-6.00%
Feed rate: rate: 45%
Disperser pressure: 2.2 bar
Auto start measurement: yes_Background measurement: 20 seconds
Sample measurement: 10 seconds Raman Spectrometry: The Raman spectrometry was recorded on a Witec Alpha 300 confocal Raman imaging system using 633nm and a Laser Helium-Neon (HeNe) 35mW. The Instrument parameters are as follows:

Laser wavelength: 532

Laser intensity (mA): 22

Integration Time (s): 0.6

Objective lens: 40×/0.6 Korr

Grating value: 600

Optical resolution (μm): 1

Example 1

Preparation of Composition Comprising Compound (A) Without the Outer Seal Coating Layer The composition is prepared by first dissolving the binder polyvinyl pyrrolidone (povidone K30), Compound (A), as defined herein, in a polar protic solvent as defined herein to provide an API solution. Said prepared API solution is then sprayed onto an inert substrate, such as lactose or Aeroperl®, in a fluid bed dryer by top spray. The mixture is then dried to remove the solvent to provide Composition comprising Compound (A), in this case a particle. Tables 1, 1A, and 2 below illustrate the composition of the particles.

TABLE 1

Preparation of Composition Comprising Compound (A) from an ethanolic solution. Formulations 1 and 2 contain Compound (A) at 0.06% and 0.1% w/w (dry basis), respectively.

| Material | Formulation 1 (F1) Quantity per Batch (g) | Formulation 2 (F2) Quantity per Batch (g) |
| --- | --- | --- |
| Spray Dried Lactose | 2000 | 2000 |
| API Solution | | |
| Compound (A) | 1.20 | 2.00 |
| Polyvinyl pyrrolidone (Povidone K30) | 1.80 | 3.00 |
| Ethanol* | 597 | 995 |
| Total | 600 | 1000 |

*The ethanol is then evaporated.

TABLE 1A

Preparation of Composition Comprising Compound (A) from an ethanolic solution. Formulations 1A and 2A each contains Compound (A) at 0.15% w/w (dry basis).

| Material | Formulation 1A (F1A) Quantity per Batch (g) | Formulation 2A (F2A) Quantity per Batch (g) |
| --- | --- | --- |
| Spray Dried Lactose | 4155.75 | |
| Spray Dried Mannitol | | 4155.75 |
| API Solution | | |
| Compound (A) | 6.75 | 6.75 |
| Polyvinyl pyrrolidone (Povidone K30) | 337.50 | 337.50 |
| Ethanol* | 4951.90 | 4951.90 |
| Total | 4500 | 4500 |

*The ethanol is then evaporated.

TABLE 2

Composition Comprising Compound (A) prepared form an aqueous suspension containing Compound (A) at 2% w/w.

| Material | Formulation 3 (F3) Quantity per Batch (g) | Formulation 4 (F4) Quantity per Batch (g) |
| --- | --- | --- |
| Inert substrate (96% w/w)** | 9.6 | 192 |
| Compound (A) (2% w/w) | 0.20 | 4.00 |
| Polyvinyl pyrrolidone (Povidone K30) (2% w/w) | 0.20 | 4.00 |
| Water* | Q.S | Q.S |
| Total | 10 | 200 |

*The water has been evaporated. Loss on drying (LOD) < 2% post processing.
**The Inert substrate can be Aeroperl ®.

Alternatively, the inert substrate, such as lactose or Aeroperl®, was pre-treated with an aqueous hydroxypropyl methylcellulose solution to achieve a granule size uniformity. Table 2A shows an example of treating the spray dried lactose with a 5% aqueous solution of HPMC. The granules of such surface treated inert substrate was then layered with a solution of Compound (A) at an appropriate concentration, and dried to achieve a loading level of 0.1% to 0.15% of Compound (A) w/w relative to the total dry weight of the composition.

TABLE 2A

Pre-treatment of spray dried lactose to provide granulated lactose.

| Material | Quantity per Batch (g) |
| --- | --- |
| Spray Dried Lactose | 4496.520 |
| HPMC solution (5% w/w) | |
| Hydroxy propyl methyl cellulose | 112.411 |
| Purified water | 2135.813 |

[1]Removed during manufacturing process.

The pre-treated (granulated) lactose was then coated with the API according to Table 2B below to provide Composition Comprising Compound (A) at 0.1% w/w (dry basis).

TABLE 2B

Composition Comprising Compound (A) at 0.1% w/w prepared from granulated lactose.

| Material | Quantity per Batch (g) |
| --- | --- |
| Granulated Lactose | 4200.004 |
| API solution (1% w/w) | |
| Polyvinyl pyrrolidone | 42.468 |
| Compound (A) | 4.247 |
| Ethanol[1] | 4642.719 |
| Dry weight | 4246.719 |

[1]Removed during manufacturing process.

Example 2

Preparation of Composition Comprising Compound (A), with Seal Coating

Composition Comprising Compound (A), prepared according to any of the formulation examples (F1, F2, F3 and F4) disclosed in Example 1, were then seal coated.

For example, the seal coating was performed by spraying a 5% w/w aqueous solution of HPMC onto the particles prepared following Formulation 2 (F2) (see Table 1), to achieve a theoretical weight gain of 3%. The Formulation 2 (F2) comprising an outer seal coating is referred to herein as Formulation F2s.

During spraying a visual inspection was performed every 30 minutes to ensure no agglomeration was occurring during the process.

Example 3

Capsule Formulations

To assess the content uniformity of each batch, the sealed coated particles comprising Compound (A) (e.g. as disclosed in Example 2) were encapsulated into size 1 capsules. The term "capsules" refer to hard gelatin capsules unless otherwise specified.

Capsules (C1) comprising 30 µg of Compound (A): In order to manufacture final dosage forms, such as capsules, containing 30 µg of Compound (A), 51.7 mg of the particles from Example 1 (Formulation 1 (F1)) was blended with 1% magnesium stearate and filled into a capsule size 1. The total weight of Compound (A) (drug load) was 0.058% of the capsule. The fill weight was adjusted accordingly.

Capsules (C2) comprising 160 µg of Compound (A): In the same manner, the final dosage forms, such as capsules, containing 160 µg dose of Compound (A), were manufactured using 166.7 mg of the particles from Example 1 (Formulation 2 (F2)) blended with 1% magnesium stearate and filled into a capsule size 1. The total weight of Compound (A) (drug load) was 0.096% of the capsule. The fill weight was adjusted accordingly.

Based on the final compositions and process parameters established from the examples outlined above, confirmatory capsule batches were manufactured using the same conditions for stability evaluation. Assay testing was performed separately on:

Particles comprising Compound (A) without the seal coating layer (F1 and F2)

Particles comprising Compound (A) and a seal coat (F1s and F2s)

Encapsulation was performed using the MG2 Labby encapsulation machine. Capsules were packaged in 30 count bottles for the stability study. The results from the confirmatory batches, including the content uniformity (CU) results, are shown in Table 3 and Table 4 below:

TABLE 3

Content uniformity results for the 30 µg capsule (C1) batch

| Sample | Formulation 1 (F1) | | F1 + outer seal coating (=F1 s) | |
|---|---|---|---|---|
| | % w/w | % LC | % w/w | % LC |
| 1 | 0.0576 | 96.1 | 0.0552 | 95.2 |
| 2 | 0.0586 | 97.7 | 0.0566 | 97.5 |
| 3 | 0.0615 | 102.4 | 0.0544 | 93.8 |
| 4 | 0.0559 | 93.2 | 0.0534 | 92.0 |
| 5 | 0.0535 | 89.1 | 0.0529 | 91.2 |
| 6 | 0.0581 | 96.9 | 0.0536 | 92.3 |

TABLE 3-continued

Content uniformity results for the 30 µg capsule (C1) batch

| Mean | 0.0580 | 95.9 | 0.054 | 93.7 |
|---|---|---|---|---|
| % RSD | 4.7 | 4.7 | 2.5 | 2.5 |
| Filter | 0.0571 | 95.1 | 0.1008 | 173.7 |

Blend filled Capsule C1 (=F1 + outer seal coating)

| Sample | % LC |
|---|---|
| 1 | 94.1 |
| 2 | 94.7 |
| 3 | 97.0 |
| 4 | 94.3 |
| 5 | 93.9 |
| 6 | 95.3 |
| 7 | 96.9 |
| 8 | 95.8 |
| 9 | 96.7 |
| 10 | 96.4 |
| Mean | 95.5 |
| % RSD | 1.2 |
| AV | 5.8 |

TABLE 4

Content uniformity results for the 160 µg capsule (C2) batch

| Sample | Formulation 2 (F2) | | F2 + outer seal coating (=F2 s) | |
|---|---|---|---|---|
| | % w/w | % LC | % w/w | % LC |
| 1 | 0.0870 | 87.0 | 0.0967 | 99.6 |
| 2 | 0.0942 | 94.2 | 0.0947 | 97.5 |
| 3 | 0.0969 | 96.9 | 0.1040 | 107.1 |
| 4 | 0.0958 | 95.8 | 0.0924 | 95.2 |
| 5 | 0.0915 | 91.5 | 0.0927 | 95.5 |
| 6 | 0.0879 | 87.9 | 0.0907 | 93.4 |
| Mean | 0.092 | 92.2 | 0.095 | 98.1 |
| % RSD | 4.5 | 4.5 | 5.0 | 5.0 |
| Filter | 0.1066 | 106.6 | 0.1645 | 169.4 |

Blend filled Capsule C2 (=F2 + outer seal coating)

| Sample | % LC |
|---|---|
| 1 | 97.7 |
| 2 | 98.5 |
| 3 | 98.0 |
| 4 | 98.3 |
| 5 | 97.6 |
| 6 | 98.1 |
| 7 | 97.7 |
| 8 | 97.4 |
| 9 | 97.5 |
| 10 | 98.8 |
| Mean | 97.9 |
| % RSD | 0.5 |
| AV | 1.7 |

As it can be seen in Table 3 and Table 4, the content uniformity results are well in the acceptable range for both the 30 µg and 160 µg dose strengths of the filled capsules. This proves a scale-able and commercially viable process was developed. In addition, both capsule strengths (C1 and C2) were tested for stability up to 12 weeks and were found to be stable with no apparent trends of change at 40° C./75% RH for both physical (dissolution) and chemical integrity.

Dissolution performance was evaluated to ensure that the dissolution profile matched that of the dry blend formulation (Compound (A), lactose, crospovidone, magnesium stearate) in a capsule. The dissolution rate is measured by the conventional method. In FIGS. 1 and 2, the dissolution rate (%) of C1, C2 and a capsule containing a dry blend comprising 0.1 mg of Compound (A) is plotted over a course of 120 min. As can be seen in FIG. 1 and FIG. 2, both dose strengths yielded dissolution greater than two times that of the dry blend formulation at 15 minutes time point. Thus, the capsule formulation of the pharmaceutical composition has the advantage to provide a formulation with fast dissolution rate, which is about 80% or more, in 20 minutes or less. This dissolution rate would meet the specification for an immediate release formulation whose dissolution rate is represented by "Q+5% Provisional."

Example 4

Tablet Formulation and Stability Data

Tablet dosage forms were developed using the Formulation 2 with a seal coating layer (F2s), as disclosed above in Example 2 and Example 3. Preliminary investigations to identify scalable and commercially viable tablet formulations indicated that a direct compression process was feasible. Two formulations were evaluated using a common blend approach and to cover the wide dose range mentioned herein. The compression profiles for both compositions were almost identical as outlined in the below examples.

TABLE 5

Tablet formulations

| Material | Formulation 5 (F5) | | | | Formulation 6 (F6) | | | |
| --- | --- | --- | --- | --- | --- | --- | --- | --- |
| | % | mg/tablet 30 µg | mg/tablet 160 µg | g/batch | % | mg/tablet 30 µg | mg/tablet 160 µg | g/batch |
| Formulation 2 sealed coated (F2 s)* | 51.54 | 30.93 | 164.95 | 154.64 | 51.54 | 30.93 | 164.95 | 154.64 |
| Drug Load Compound (A) | 0.05 | 0.03 | 0.16 | | 0.05 | 0.03 | 0.16 | |
| Lactose SD | 28.45 | 17.07 | 91.05 | 85.36 | 15 | 9 | 48 | 45 |
| Mannitol DC | 15 | 9 | 48 | 45 | 28.45 | 17.07 | 91.05 | 85.36 |
| Croscarmellose Sodium (Ac-Di-Sol) | 3 | 1.80 | 9.60 | 9 | 3 | 1.80 | 9.60 | 9 |
| Aerosil | 1 | 0.60 | 3.20 | 3 | 1 | 0.60 | 3.20 | 3 |
| Magnesium Stearate | 1 | 0.60 | 3.20 | 3 | 1 | 0.60 | 3.20 | 3 |
| Total | 100 | 60 | 320 | 300 | 100 | 60 | 320 | 300 |

*Drug load Compound A = 0.097%

Formulation 6 at both dose strengths was manufactured in a larger scale and was film coated using standard Opadry® brown film coat. Opadry® is a complete film coating system made by Colorcon and it is Colorcon's customized one-step system that combines polymer, plasticizer and pigment in a dry concentrate. The analytical results from these batches are disclosed in Table 6 (below), and are depicted in FIG. 4, and FIG. 5.

TABLE 6

Dissolution and content uniformity results of the film coated tablet

| Test | Specification | | Compound (A) 30 µg film coated tablets Tablet 1 (T1) | Compound (A) 160 µg film coated tablets Tablet 2 (T2) |
| --- | --- | --- | --- | --- |
| Assay | 90.0-110.0% of Label Claim (LC) | | 104.28% | 104.10% |
| | | Time Point | | |
| Dissolution | As per USP <711> and Ph. Eur. 2.9.3 (Q = 70%) after 90 minutes | 15 min | 102 | 100 |
| | | 30 min | 104 | 103 |
| | | 45 min | 104 | 103 |
| | | 60 min | 104 | 103 |
| | | 75 min | 104 | 103 |
| | | 90 min | 104 | 103 |
| | | 120 min | 104 | 103 |
| | | Content Uniformity (CU) Preparation | | |
| Content Uniformity | Uniformity of Dosage Units (by Content Uniformity) | 1 | 104.52 | 105.21 |
| | | 2 | 103.97 | 103.99 |
| | | 3 | 103.46 | 101.64 |

TABLE 6-continued

Dissolution and content uniformity results of the film coated tablet

| Test | Specification | | Compound (A) 30 μg film coated tablets Tablet 1 (T1) | Compound (A) 160 μg film coated tablets Tablet 2 (T2) |
|---|---|---|---|---|
| | must comply with | 4 | 101.71 | 102.90 |
| | Eur. Ph. 2.9.40 | 5 | 102.76 | 101.60 |
| | Acceptance Value | 6 | 103.30 | 102.22 |
| | (AV) less than or | 7 | 101.72 | 102.80 |
| | equal to 15.0 | 8 | 103.07 | 101.89 |
| | | 9 | 103.41 | 103.24 |
| | | 10 | 102.49 | 101.30 |
| | | Mean | 103.0 | 102.7 |
| | | RSD % | 0.8 | 1.2 |
| | | AV | 3.7 | 4.1 |

Dissolution performance was evaluated to ensure that the dissolution profile matched that of the dry blend formulation (Compound (A) encapsulated in a capsule, same as in Example 3). The dissolution rate rate is measured by the conventional method. FIG. 4 and FIG. 5 summarize the dissolution profiles of the tablets comprising the above formulations (Formulation 5 and Formulation 6), compressed at different compression forces (2 KN and 11 KN). The fast dissolution observed for the capsule formulation (see FIG. 2 and FIG. 3) was not impacted by the compression of the blend into tablets. Surprisingly, the dissolution rate observed with the tablet formulations is even faster than the dissolution rate of the capsule formulations. As it can be seen in FIG. 4 and FIG. 5, the tablet formulations have the advantage to provide a formulation with a dissolution rate of about 85% or more, in 20 minutes or less. Both strengths (30 μg and 160 μg) made using Formulation 6 were film-coated and stability assays were performed on the corresponding film-coated tablets (Tablet 1 (T1) and Tablet 2 (T2) as seen in Table 6). The results are depicted in Table 7 and Table 8 below.

TABLE 7

Assay stability data of Tablet 1 (T1)

| Time (weeks) | 0 | 3 | 6 | 24 |
|---|---|---|---|---|
| 40° C./75% RH | 104.3% | 103.6% | 104.6% | 103.9% |
| Dissolution* | 104% | 105% | 106% | 103% |

*As per (USP<711> and Ph. Eur. 2.9.3) Q = 70% after 90 minutes

TABLE 8

Assay stability data of Tablet 2 (T2)

| Time (weeks) | 0 | 3 | 6 | 24 |
|---|---|---|---|---|
| 40° C./75% RH | 104.1% | 103.5% | 105.2% | 105.3% |
| Dissolution* | 103% | 103% | 103% | 102% |

*As per (USP<711> and Ph. Eur. 2.9.3) Q = 70% after 90 minutes

After 24 weeks, the stability results, as shown in Table 7 and Table 8, confirm the stability of the drug product and no degradation is observed. As can be seen in Table 7 and Table 8, the dissolution performance of the film-coated tablet is not compromised even under these conditions.

Example 5

DSC, PSD, XRPD, SEM Analysis and Raman Spectroscopy

Differential Scanning calorimetry (DSC), Particle Size Distribution (PSD) and X-ray Powder Diffraction (XRPD), Scanning Electron Microscopy (SEM) analysis, and Raman spectrometry were carried out on the materials used for the development of the tablet formulations comprising Compound (A), as depicted in Formulation 5 and Formulation 6. These experiments helped to characterize and determine the physical nature of Compound (A).

FIG. 6 shows the XRPD diffractograms for the lactose (commercially available—spray dried grade) as inert substrate, the seal coated Formulation 2 (referred herein as F2s), and the common blend prepared according to Table 5, Formulation 6. Comparing all peaks together, the additional peaks present in the diffractogram of the final blend can be attributed to Mannitol DC (~11.5, 14.6, 16.8, 18.8, 20.5, 21.1, 21.7, 23.4, 25.9, 26.1, 29.5, 30.6, 33.6, 33.7, 33.9, and 36.1° (2 θ degrees).

FIG. 7 shows the DSC thermogram used to determine the thermal profile of the sealed coated Formulation 2 (F2s) from about 30° C. to 300° C. at 10° C./minute. The thermogram shows two distinct endotherms, which may be attributable to melting of multiple components. The first endotherm (onset temperature about 134° C.) is broad, exhibiting both peak fronting and tailing, suggesting at least 3 components are present. Decomposition is evident towards the end of the second endotherm at about 240° C. The thermal data generated for the sample is reported in Table 9 below.

TABLE 9

DSC thermal data obtained for the sealed coated formulation F2 (F2 s)

| Sample Description | Endotherm 1 (° C.) | | | Endotherm 2 (° C.) | | |
|---|---|---|---|---|---|---|
| | Onset Temp. (° C.) | Heat Flow (J/g) | Peak Temp. (° C.) | Onset Temp. (° C.) | Heat Flow (J/g) | Peak Temp. (° C.) |
| F2 s | 134.48 | 140.5300 | 140.60 | 209.99 | 278.2691 | 218.56 |

FIG. 8 and FIG. 9 show particle size distribution of the seal coated Formulation 2 (F2s) and the Formulation 6 (F6), which were determined by laser diffraction using dry dispersion. Particle size analysis for each sample was performed in triplicate. The mean particle size data determined for the Dv10, Dv50 and Dv90 are reported in Table 10 below:

TABLE 10

Particle size data determined for the particle made according to the Formulation 2 (F2) and the Formulation 6

| Material | Prep# | μm | | |
|---|---|---|---|---|
| | | Dv10 | Dv50 | Dv90 |
| Seal Coated | 1 | 115.669 | 173.540 | 254.715 |
| Formulation 2 | 2 | 117.853 | 169.732 | 241.322 |
| (F2 s) | 3 | 120.457 | 173.614 | 248.519 |
| | Mean | 117.99 | 172.30 | 248.19 |
| | % RSD | 2 | 1 | 3 |
| Formulation 6 | 1 | 60.253 | 153.844 | 261.210 |
| (F6) | 2 | 67.160 | 152.807 | 255.700 |
| | 3 | 66.476 | 151.540 | 257.340 |
| | Mean | 64.63 | 152.73 | 258.08 |
| | % RSD | 6 | 1 | 1 |

The XRPD and DSC results alone were unable to distinguish the physical nature of Compound (A) due to the extremely low drug concentration of 0.1% and the presence of other excipients especially in the blend used for the tablet dosage form. In view of this, additional investigations were conducted, such as SEM analysis.

The SEM analysis was performed on the following samples:
Lactose (commercially available—spray dried grade)
Formulation 2, as disclosed herein
Seal Coated Formulation 2 (F2s)

SEM images of each of the above batches are shown in FIGS. 10 to 15. In FIG. 11, crystals of Compound (A) are visible relative to FIG. 10, the Lactose without Compound (A), FIGS. 11 to 14 show the appearance of the Formulation 2 (F2) and the seal coated Formulation F2 (F2s), as disclosed herein, at two different resolutions. The seal coated particles of the Formulation 2 (F2s) have a smooth surface compared to the particles of the Formulation 2 (F2) without the seal coating layer. This demonstrates that the seal coating was effective.

To confirm the crystalline nature of the drug, Raman microscopy and analysis were investigated to determine the spatial distribution on the (a) inert substrate, in this case lactose. This study aimed at determining the spatial distribution of compound (A), in the Formulation 2 (F2), once dispersed onto the inert substrate (drug load of 0.1% and PVPK30 as binder). A suitable amount of particles were deposited onto a microscopy slide and a single surface Raman mappings (150×150 μm²-1 μm resolution/0.6 s second integration time) was performed. Scanning the sample surface and mapping Raman spectra across the scanned area showed clearly defined (microparticle-like) areas where spectra could be associated with crystalline Compound (A), while in-between those areas the Raman spectra were associated with excipients (binder, carrier) only (as seen in FIG. 16 and FIG. 17).

Samples of crystalline Compound (A) and amorphous Compound (A) were prepared from pure compound (A), and were used as a comparison Reference.

The crystalline Compound (A) was prepared according to well known in the art crystallisation technique.

Amorphous Compound (A) was prepared as followed: 30 mg of Compound (A) was dissolved in 1.5 mL of dioxane in 2 separate vials. The vials were shock frozen in dry ice. Lyophilisation was performed overnight, using techniques well known in the art, until amorphous Compound (A) was obtained. The amorphous sample was analysed using XRPD/DSC.

Those samples were analysed by Raman spectroscopy (see FIG. 18, so called "Compound (A) crystalline reference" and "Compound (A) amorphous reference"). Raman spectra of reference crystalline Compound (A) and amorphous Compound (A) were compared to that of Compound (A) extracted from the Formulation 2 (F2). As seen in FIG. 18, Compound (A) layered onto the inert substrate (e.g lactose), according to the Formulation 2 (F2), exhibits clear correlation with the Raman fingerprint of "Compound (A) crystalline reference" in terms of characteristic Raman peak positions. Thus, showing that Compound (A) can also be present in a crystalline form in the pharmaceutical composition.

Example 6

Compound (A) for the Treatment of Nonalcoholic Steatohepatitis—Interim Results Based on Baseline Body Mass Index from Phase 2b Study FLIGHT-FXR The FLIGHT-FXR (NCT02855164) is a Phase 2, randomized, double-blind, multicenter, placebo-controlled trial with an adaptive design to assess the safety, tolerability, and efficacy of Compound (A) in patients with NASH (nonalcoholic steatohepatitis). Data from Compound (A) 60 μg, Compound (A) 90 μg, and placebo arms are provided herein-below.

Patients were divided into two subgroups: Lower BMI subgroup (BMI <30 kg/m² (Asian) or <35 kg/m² (Non-Asian)) and Higher BMI subgroup (BMI ≥30 kg/m² (Asian) or ≥35 kg/m² (Non-Asian))

The objectives of the study were as follows:
To determine the dose-response relationship of compound (A) on a marker of FXR target engagement in the gut (FGF19) by BMI subgroups over time.
To determine dose-response relationship of compound (A) on markers of hepatic inflammation (alanine aminotransferase [ALT]), target engagement and marker of oxidative stress (gamma-glutamyl transferase [GGT]), and on changes in liver fat content (LFC) measured by magnetic resonance imaging proton density fat fraction (MRI-PDFF) at Week 12 by BMI subgroups.
To determine lipids profile by BMI subgroups.

TABLE 11

Study population

| Key inclusion criteria | Key exclusion criteria |
|---|---|
| Male and female patients aged ≥18 years, weighing ≥40 and ≤150 kg | History of liver transplantation |
| Liver fat content ≥10% at screening | Uncontrolled diabetes mellitus (DM) defined as HbA1c ≥9.5% within 60 days prior to enrolment |

TABLE 11-continued

Study population

| Key inclusion criteria | Key exclusion criteria |
|---|---|
| Presence of NASH was defined by:<br>Liver biopsy consistent with NASH and fibrosis level F1, F2, or F3, obtained 2 years or less prior to randomisation, no diagnosis of alternate chronic liver disease and elevated ALT (≥43 IU/L [males] or ≥28 IU/L [females]) OR<br><br>Phenotypic diagnosis based on all of the following: elevated ALT (≥43 IU/L [males] or ≥28 IU/L [females]), BMI ≥27 kg/m$^2$ (in patients with a self-identified race other than Asian) or ≥23 kg/m$^2$ (in patients with a self-identified Asian race), and diagnosis of Type 2 diabetes mellitus (DM) by having either glycocylated haemoglobin (HbA1c) ≥6.5% or drug therapy for Type 2 DM | Prior diagnosis of other forms of chronic liver disease, presence of cirrhosis on liver biopsy, or clinical diagnosis of cirrhosis and/or platelet count <120 × 109/L or severe liver impairment Current or history of significant alcohol consumption (male, >30 g/day; female, >20 g/day, on average) for a period of >3 consecutive months within 1 year prior to screening and/or a score on the AUDIT questionnaire ≥8<br>Pregnant or nursing (lactating) mothers<br>Previous exposure to obeticholic acid |

Results and Efficacy of 60 μg Compound (A), 90 μg Compound (A), and Placebo

Table 12 (below) shows the results observed in each treatment arms.

TABLE 12

Geometric mean percentage change in markers of efficacy (FGF19 (4 hours post-dose from pre-dose at Week 6) and all others parameters from baseline to Week 12)) by BMI subgroups (with N, total number of patients)

| | Lower BMI† | | | Higher BMI‡ | | |
|---|---|---|---|---|---|---|
| Parameters, % | Placebo<br>N = 28 | Compound (A),<br>60 μg<br>N = 21 | Compound (A),<br>90 μg,<br>N = 52 | Placebo<br>N = 18 | Compound (A),<br>60 μg<br>N = 16 | Compound (A),<br>90 μg<br>N = 33 |
| FGF19 | 21.5 | 360.2 | 585.8 | 68.0 | 276.9 | 446.9 |
| C4 | 2.8 | −33.2 | −40.4 | 37.3 | −48.9 | −61.8 |
| GGT | −10.8 | −47.0 | −61.3 | −6.8 | −38.4 | −48.7 |
| ALT | −18.6 | −26.0 | −26.8 | −10.6 | −14.8 | −19.5 |
| LFC§ | −13.1 | −19.9 | −18.8 | −5.5 | −12.9 | −11.4 |
| HDL-C | −4.8 | −1.9 | −7.7 | −3.9 | −6.1 | −11.9 |
| TG | 1.2 | 0.9 | 5.7 | 0.9 | −6.7 | −2.3 |

†BMI < 30 kg/m$^2$ (Asian) or <35 kg/m$^2$ (Non-Asian);
‡BMI ≥ 30 kg/m$^2$ (Asian) or ≥35 kg/m$^2$ (Non-Asian);
§Measured by MRI-PDFF Effect of Compound (A) on marker of target engagement: FGF19: the assessment of FGF19 was done at Week 6. A dose-response increase in the FGF19 levels was observed 4 hours post-dose compared with pre-dose in both BMI subgroups. At Week 6, the geometric mean percentage changes in FGF19 from pre-dose in the lower BMI subgroup (60 μg of Compound (A)=360.2, and 90 μg of Compound (A)=585.8) were higher than the mean percentage changes in the higher BMI subgroup (60 μg of Compound (A)=276.9, and 90 μg of Compound (A)=446.9).

Effect of Compound (A) on marker of hepatic inflammation: ALT: A rapid and sustained decline in ALT levels from baseline was observed with 90 μg of Compound (A) doses in patients from both BMI subgroups, more marked in the group with lower BMI.

Effect of Compound (A) on GGT, a marker of oxidative stress: A dose-response decrease in GGT levels was observed with Compound (A) in both BMI subgroups, more marked in the group with lower BMI. At Week 12, the geometric mean percentage change in GGT was higher with 60 μg of Compound (A) (−47.0) and 90 μg of Compound (A) (−61.3) in the lower BMI versus 60 μg of Compound (A) (−38.4) and 90 μg of Compound (A) (−48.7) in the higher BMI subgroup.

Effect of Compound (A) on liver fat content: At Week 12, the mean percentage change was greater in all arms in the lower BMI subgroup (placebo=−13.1; Compound (A) 60 μg=−19.9, and Compound (A) 90 μg=−18.8) compared with the higher BMI subgroup (placebo=−5.5; Compound (A) 60 μg=−12.9, and Compound (A) 90 μg=−11.4). The proportion of patients with an absolute decrease of Liver fat content (LFC) by >5% was higher in the lower BMI subgroup versus the higher BMI subgroup.

Effect of Compound (A) on C4: At Week 12, a decrease of 7-hydroxy-4-cholesten-3-one (C4) was observed in all Compound (A) treatment groups. This decrease is more obvious in the higher BMI subgroup. However, C4 is subject to diurnal variation, therefore, the influence of BMI on C4 invites further investigation.

As far as the safety of the formulation comprising Compound (A) is concerned, the Incidence of adverse events, including pruritus, was comparable between arms. Lipid profiles were comparable in both BMI subgroups. The interim results from the first two parts of this Phase 2b study provide the evidence for target engagement, anti-inflammatory, and antisteatotic effects of Compound (A) in both BMI subgroups. However, the effect of Compound (A) on ALT, GGT, and LFC was more pronounced in the lower BMI subgroup. The study also showed that the lipid profiles were comparable in both subgroups and that rates of events in the study, including pruritus, were comparable across treatment arms. Consistent trends of lower responses in the higher BMI subgroup, receiving lower dosing by body weight, support testing higher Compound (A) doses (e.g. 140 and 200 µg/day).

Example 7

Absorption, Distribution, Metabolism, and Excretion of Compound (A), Following a Single 1-mg Oral Dose of [$^{14}$C] Compound (A) in Healthy Human Subjects Absorption, distribution, metabolism, and excretion of Compound (A) was studied following a single 1-mg oral dose of [$^{14}$C]Compound (A) to four healthy human subjects. The rate and route of excretion of [$^{14}$C]Compound (A) related radioactivity was determined as well as pharmacokinetic profiles of Compound (A) and of total radioactivity in plasma. The key biotransformation pathways and clearance mechanisms of [$^{14}$C]Compound (A) in human were elucidated. Mass balance was achieved with approximately 94% of the administered dose recovered in excreta through the 312 hours collection period. Faecal excretion of Compound (A) related radioactivity played a major role (approximatively 65% of the total dose) while urinary excretion played a slightly minor role (approximatively 29% of the total dose). After oral administration of 1 mg [$^{14}$C]Compound (A) to human subjects, parent Compound (A) reached a maximum concentration (Cmax) of 33.5 ng/mL with a median Tmax (time the maximum concentration is reached) of 4 hours and eliminated with a half time ($t^{1/2}$) of 13.5 hours in plasma. Unchanged Compound (A) was the principal drug-related component found in the plasma (approximatively 92% of total radioactivity). Two minor oxidative metabolites, were observed in circulation, at approximatively 2% and approximatively 5% of the total drug radioactivity exposure, respectively. Compound (A) was eliminated predominantly via metabolism with more than 68% of the dose recovered as metabolites in excreta. Oxidative metabolism appeared to be the major clearance pathway of Compound (A) as the majority of the radioactivity observed in human excreta consisted of oxidative metabolites. Primary phase 1 oxidative pathways included:

1) oxidative O-dealkylation; 2) oxidation at the phenyl cyclopropyl isoxazole moiety; 3) oxidation at the benzothiazole and fused ring structure. Metabolites containing multiple oxidative modifications and/or glucuronidation to oxidative products were also observed in human excreta.

Example 8

In Vivo PK

The PK profiles of the Compound (A) drug products were evaluated in male beagle dogs according to the following method:

Drug substance: Compound (A);

Drug products: S1—hard gelatin capsules, S2—soft gelatin capsules, and S3—film coated tablets according to the compositions below:

| S1 | mg/unit |
|---|---|
| Compound (A) | 0.03 |
| Lactose | 28.92 |
| Crospovidone | 0.9 |
| Magnesium stearate | 0.15 |
| Capsule | 48 |

| S2 | mg/unit |
|---|---|
| Compound (A) | 0.03 |
| Propylene glycol monolaurate | 139.97 |
| Glycerol | 35.64 |
| Gelatin | 67.49 |
| Purified water | 48.53 |
| Titanium dioxide | 1.52 |
| Glycerol | 1.52 |
| Purified water | 0.3 |

| S3 | mg/unit |
|---|---|
| Formulation 2 | 30.09 (30 µg Compound (A)) |
| Lactose | 9 |
| Mannitol | 17.1 |
| Croscarmellose Sodium | 1.8 |
| Silicon dioxide | 0.6 |
| Magnesium stearate | 0.6 |
| HPMC Coating | 5 |

Species, strain, sex: beagle dog, male (n=4), crossover;

Route of administration: Oral (pentagastrin pre-treatment (6 µg/kg i.m.) 30 min prior to dosing);

Feeding status: Fasted overnight prior to dose administration. Food was returned to the animals after 4 h sample collection;

Dose: 30 µg/animal/dose;

Sample collected: K$_2$-EDTA Blood (plasma analyzed);

Sampling time points: 0.25, 0.5, 1, 2, 3, 5, 8, 24, 28 and 32 h post dose;

Sample analysis: LC-MS/MS with positive electrospray ionization.

The PK results are summarized in Table 13 below.

TABLE 13

PK properties of certain embodiments of the invention

| Drug Product | S1 | S2 | S3 |
|---|---|---|---|
| Dose | 0.00313 ± 0.000439 | 0.00313 ± 0.000445 | 0.00315 ± 0.000470 |
| Tmax$^a$ (h) | 3.0 [2-24] | 3.0 [2-8] | 3.0 [2-5] |
| Tlast$^a$ (h) | 32 [32-32] | 32 [32-32] | 32 [32-32] |
| Cmax (ng/mL) | 1.71 ± 0.740 | 2.89 ± 0.871 | 3.37 ± 0.974 |
| Cmax/dose (ng/mL)/(mg) | 57.0 ± 24.7 | 96.4 ± 29.0 | 112 ± 32.5 |

TABLE 13-continued

PK properties of certain embodiments of the invention

| Drug Product | S1 | S2 | S3 |
|---|---|---|---|
| AUClast (h*ng/mL) | 24.1 ± 6.65 | 43.9 ± 6.71 | 36.2 ± 5.60 |
| AUClast/dose (hr*ng/mL/mg) | 802 ± 222 | 1460 ± 224 | 1210 ± 187 |
| AUCinf (h*ng/mL) | 27.5 ± 7.60 | 46.7 ± 7.64 | 41.6 ± 4.56 |
| AUCinf/dose (h*ng/mL)/(mg) | 916 ± 253 | 1560 ± 255 | 1390 ± 152 |
| Bioavailability (%) | 100 | 192 ± 49.8 | 157 ± 38.6 |

[a]Median [range].

The average plasma concentration profile of the three examples are graphed in FIG. 19. As shown in Examples 3 and 4, the current invention provides a composition with a superior in vitro dissolution profile of Compound (A) relative to the dry blend composition. The superior dissolution is manifested in the higher bioavailability in vivo in the dog as demonstrated here.

The invention claimed is:

1. A pharmaceutical composition for oral administration comprising (a) an inert substrate, and (b) a mixture comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, as an active pharmaceutical ingredient, and at least one binder.

2. The pharmaceutical composition of claim 1, wherein 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid is in a free form.

3. The pharmaceutical composition of claim 1, wherein the (a) inert substrate comprises a material selected from the group consisting of lactose, microcrystalline cellulose, mannitol, sucrose, starch, granulated hydrophilic fumed silica, and mixtures thereof.

4. The pharmaceutical composition of claim 1, wherein the binder is selected from the group consisting of polyvinyl pyrrolidone, hydroxypropyl cellulose, hydroxypropyl methylcellulose, carboxymethyl cellulose, methyl cellulose, hydroxyethyl cellulose, carboxyethyl cellulose, carboxymethylhydroxyethyl cellulose, polyethylene glycol, polyvinyl alcohol, shellac, polyvinyl alcohol-polyethylene glycol co-polymer, and mixtures thereof.

5. The pharmaceutical composition of claim 1, wherein the pharmaceutical composition is a particle.

6. The pharmaceutical composition according to claim 5, wherein the particle further comprises (c) an outer seal coating layer.

7. The pharmaceutical composition according to claim 6, wherein the outer seal coating layer is selected from the group consisting of hydroxypropyl methyl cellulose, polyvinyl pyrrolidone, hydroxypropyl cellulose, carboxymethyl cellulose, methyl cellulose, hydroxyethyl cellulose, carboxyethyl cellulose, carboxymethylhydroxyethyl cellulose, polyethylene glycol, polyvinyl alcohol, and mixtures thereof.

8. The pharmaceutical composition according to claim 1, further comprising at least one additional active pharmaceutical ingredient.

9. A final dosage form comprising the pharmaceutical composition according to claim 1, wherein the final dosage form is a capsule, a tablet, a mini-tablet, a sachet, or a stickpack.

10. The final dosage form according to claim 9, wherein the final dosage form is a capsule or a tablet.

11. The final dosage form according to claim 9, comprising 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of about 0.01 mg to about 2 mg.

12. A process for preparing a pharmaceutical composition for oral administration comprising an inert substrate, 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, as an active pharmaceutical ingredient, and at least one binder, the process comprising the steps of:
(i) mixing the 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, the at least one binder, and optionally at least one protic polar solvent, to form a mixture; and
(ii) adding the mixture of step (i) to the inert substrate.

13. The process of claim 12, wherein step (i) comprises mixing the 2-[(1R,3r,5S)-3-({5-cyclopropyl-3-[2-(trifluoromethoxy)phenyl]-1,2-oxazol-4-yl}methoxy)-8-azabicyclo[3,2,1]octan-8-yl]-4-fluoro-1,3-benzothiazole-6-carboxylic acid, or a pharmaceutically acceptable salt thereof, the at least one binder, and further at least one protic polar solvent to form the mixture, wherein the process further comprises the step of:
(iii) removing the at least one protic polar solvent.

14. The process of claim 13, wherein the at least one protic polar solvent is selected from the group consisting of organic solvents, water, and mixtures thereof.

15. The process of claim 14, wherein the organic solvent is selected from the group consisting of methanol, ethanol, isopropanol, n-propanol, n-butanol, and mixtures thereof.

16. The process of claim 12, wherein in step (ii) adding the mixture of step (i) to the inert substrate comprises dispersing the mixture of step (i) onto the (a) inert substrate.

17. The process of claim 12, wherein in step (ii) adding the mixture of step (i) to the inert substrate comprises coating the inert substrate with the mixture of step (i).

18. The process of claim 12, wherein the pharmaceutical composition is a particle, and wherein the process further comprises the step of adding an outer seal coating layer onto the particle.

19. The process according to claim 12, further comprising the step of adding at least one additional active pharmaceutical ingredient.

20. A method of treating a disease or disorder in a patient in need thereof, wherein the disease or disorder is selected from the group consisting of cholestasis, intrahepatic cholestatis, estrogen-induced cholestasis, drug-induced cholestasis, cholestasis of pregnancy, parenteral nutrition-associated cholestasis, primary biliary cirrhosis, non-alcoholic fatty liver disease, non-alcoholic steatohepatitis, liver cirrhosis, alcohol-induced cirrhosis, cystic fibrosis, and liver fibrosis, comprising the step of administering to the patient an effective amount of the pharmaceutical composition of claim 1.

* * * * *